US011413347B2

(12) United States Patent
Chang et al.

(10) Patent No.: US 11,413,347 B2
(45) Date of Patent: Aug. 16, 2022

(54) VACCINE COMPOSITION AND METHOD OF PREVENTING PORCINE EPIDEMIC DIARRHEA VIRUS INFECTION IN SWINE

(71) Applicant: Reber Genetics Co., Ltd., Taipei (TW)

(72) Inventors: Chia-Jung Chang, Kaohsiung (TW); Jen-Yu Chang, Taoyuan (TW); Cheng-Xin Yang, Taoyuan (TW)

(73) Assignee: Reber Genetics Co., Ltd., Taipei (TW)

( * ) Notice: Subject to any disclaimer, the term of this patent is extended or adjusted under 35 U.S.C. 154(b) by 0 days.

(21) Appl. No.: 17/000,377

(22) Filed: Aug. 24, 2020

(65) Prior Publication Data

US 2021/0060154 A1 Mar. 4, 2021

Related U.S. Application Data

(60) Provisional application No. 62/894,867, filed on Sep. 2, 2019.

(51) Int. Cl.

| | |
|---|---|
| ***A61K 39/225*** | (2006.01) |
| ***C12N 7/00*** | (2006.01) |
| ***A61K 39/39*** | (2006.01) |
| *A61K 39/00* | (2006.01) |

(52) U.S. Cl.

CPC ............ *A61K 39/225* (2013.01); *A61K 39/39* (2013.01); *C12N 7/00* (2013.01); *A61K 2039/5252* (2013.01); *A61K 2039/552* (2013.01); *C12N 2770/20034* (2013.01)

(58) Field of Classification Search

CPC ............ A61K 39/215; A61K 2039/552; A61K 2039/53; A61K 2300/00; A61K 39/12; A61K 45/06; A61K 2039/55555; A61K 2039/55566; A61K 2039/522; A61P 31/14; A61P 37/04; A61P 31/12; C07K 14/165; C07K 16/10; C12N 2750/14143; C12N 2770/20034; C12N 2750/14152; C12N 15/1034; C12N 15/1093; C12N 15/11; C12N 15/113; C12N 15/62; C12N 1/205; C12N 2310/322; C12N 2310/3521; C12N 2310/3525; C12N 2310/3533; C12N 2320/32; C12N 2750/14142; C12N 2750/14171; C12N 2770/20071; C12N 9/1276; C12N 9/78; C12N 15/111; C12N 15/8645; C12N 15/907; C12N 1/20; C12N 2310/11; C12N 2310/14; C12N 2740/13034; C12N 2740/16043; C12N 2750/14145; C12N 7/00; C12N 15/86; C12N 2760/16234; C12N 2760/18522; C12N 2760/18571

See application file for complete search history.

(56) References Cited

U.S. PATENT DOCUMENTS

| | | | | |
|---|---|---|---|---|
| 10,280,199 | B2 * | 5/2019 | Kim | A61K 39/12 |
| 2018/0064804 | A1 | 3/2018 | Zhang et al. | |
| 2019/0202868 | A1 * | 7/2019 | Kim | C07K 14/005 |

FOREIGN PATENT DOCUMENTS

| | | |
|---|---|---|
| CN | 107073101 | 8/2017 |
| TW | 201613558 | 4/2016 |
| TW | 201641689 | 12/2016 |
| TW | 201825114 | 7/2018 |

OTHER PUBLICATIONS

"Office Action of Taiwan Counterpart Application", dated Oct. 4, 2021, p. 1-p. 8.

J.-Y. Peng et al., "Different intestinal tropism of the G2b Taiwan porcine epidemic diarrhea virus-Pintung 52 strain in conventional 7-day-old piglets," The Veterinary Journal, vol. 237, Jun. 7, 2018, pp. 69-75.

Yen-Chen Chang et al., "Efficacy of heat-labile enterotoxin B subunit-adjuvanted parenteral porcine epidemic diarrhea virus trimeric spike subunit vaccine in piglets," Appl Microbiol Biotechnol., vol. 102, No. 17, Jun. 30, 2018, pp. 7499-7507.

H.-Y. Chiou et al., "Phylogenetic Analysis of the Spike (S) Gene of the New Variants of Porcine Epidemic Diarrhoea Virus in Taiwan," Transbound Emerg Dis., vol. 64, No. 1, Apr. 22, 2015, pp. 1-10.

Hui-Wen Chang et al., "Spike Protein Fusion Peptide and Feline Coronavirus Virulence," Emerg Infect Dis , vol. 18, No. 7, Jul. 2012, pp. 1089-1095.

Chi-Fei Kao et al., "The Characterization of Immunoprotection Induced by a cDNA Clone Derived from the Attenuated Taiwan Porcine Epidemic Diarrhea Virus Pintung 52 Strain," Viruses, vol. 10, Oct. 4, 2018, pp. 1-15.

Tsung-Lin Tsai et al., "Gene Variations in Cis-Acting Elements between the Taiwan and Prototype Strains of Porcine Epidemic Diarrhea Virus Alter Viral Gene Expression," Genes, vol. 9, Nov. 29, 2018, pp. 1-16.

* cited by examiner

*Primary Examiner* — Bao Q Li
(74) *Attorney, Agent, or Firm* — JCIPRNET

(57) ABSTRACT

A vaccine composition includes a porcine epidemic diarrhea virus (PEDV) S1 spike protein having an amino acid sequence of SEQ ID NO: 1, and an inactivated porcine epidemic diarrhea virus (PEDV). The vaccine composition is used in a method of preventing PEDV infection in swine, whereby systemic Immunoglobulin G (IgG), Immunoglobulin A (IgA) and neutralizing antibody may be successfully induced by the vaccine composition, hence providing sufficient immune protection against PEDV.

7 Claims, 6 Drawing Sheets

Specification includes a Sequence Listing.

Neutralizing antibody

Neutralizing antibody dilution factor 700
600
500
400
300
200
100
0

SEQUENCE LISTING

```
<160> NUMBER OF SEQ ID NOS: 4

<210> SEQ ID NO 1
<211> LENGTH: 725
<212> TYPE: PRT
<213> ORGANISM: porcine epidemic diarrhea virus
```

```
<400> SEQUENCE: 1

Cys Ser Ala Asn Thr Asn Phe Arg Arg Phe Phe Ser Lys Phe Asn Val
1               5                   10                  15

Gln Ala Pro Ala Val Val Val Leu Gly Gly Tyr Leu Pro Ile Gly Glu
            20                  25                  30

Asn Gln Gly Val Asn Ser Thr Trp Tyr Cys Ala Gly Gln His Pro Thr
        35                  40                  45

Ala Ser Gly Val His Gly Ile Phe Val Ser His Ile Arg Gly Gly His
    50                  55                  60

Gly Phe Glu Ile Gly Ile Ser Gln Glu Pro Phe Asp Pro Ser Gly Tyr
65                  70                  75                  80

Gln Leu Tyr Leu His Lys Ala Thr Asn Gly Asn Thr Asn Ala Thr Ala
                85                  90                  95

Arg Leu Arg Ile Cys Gln Phe Pro Ser Ile Lys Thr Leu Gly Pro Thr
            100                 105                 110

Ala Asn Asn Asp Val Thr Thr Gly Arg Asn Cys Leu Phe Asn Lys Ala
        115                 120                 125

Ile Pro Ala His Met Ser Glu His Ser Val Val Gly Ile Thr Trp Asp
    130                 135                 140

Asn Asp Arg Val Thr Val Phe Ser Asp Lys Ile Tyr Tyr Phe Tyr Phe
145                 150                 155                 160

Lys Asn Asp Trp Ser Arg Val Ala Thr Lys Cys Tyr Asn Ser Gly Gly
                165                 170                 175

Cys Ala Met Gln Tyr Val Tyr Glu Pro Thr Tyr Tyr Met Leu Asn Val
            180                 185                 190

Thr Ser Ala Gly Glu Asp Gly Ile Ser Tyr Gln Pro Cys Thr Ala Asn
        195                 200                 205

Cys Ile Gly Tyr Ala Ala Asn Val Phe Ala Thr Glu Pro Asn Gly His
    210                 215                 220

Ile Pro Glu Gly Phe Ser Phe Asn Asn Trp Phe Leu Leu Ser Asn Asp
225                 230                 235                 240

Ser Thr Leu Val His Gly Lys Val Val Ser Asn Gln Pro Leu Leu Val
                245                 250                 255

Asn Cys Leu Leu Ala Ile Pro Lys Ile Tyr Gly Leu Gly Gln Phe Phe
            260                 265                 270

Ser Phe Asn Gln Thr Ile Asp Gly Val Cys Asn Gly Ala Ala Val Gln
        275                 280                 285

Arg Ala Pro Glu Ala Leu Arg Phe Asn Ile Asn Asp Thr Ser Val Ile
    290                 295                 300

Leu Ala Glu Gly Ser Ile Val Leu His Thr Ala Leu Gly Thr Asn Phe
305                 310                 315                 320

Ser Phe Val Cys Ser Asn Ser Ser Asn Pro His Leu Ala Thr Phe Ala
                325                 330                 335

Ile Pro Leu Gly Ala Thr Gln Val Pro Tyr Tyr Cys Phe Phe Lys Val
            340                 345                 350

Asp Thr Tyr Asn Ser Thr Val Tyr Lys Phe Leu Ala Val Leu Pro Pro
        355                 360                 365

Thr Val Arg Glu Ile Val Ile Thr Lys Tyr Gly Asp Val Tyr Val Asn
    370                 375                 380

Gly Phe Gly Tyr Leu His Leu Gly Leu Leu Asp Ala Val Thr Ile Asn
385                 390                 395                 400

Phe Thr Gly His Gly Thr Asp Asp Asp Val Ser Gly Phe Trp Thr Ile
                405                 410                 415
```

```
Ala Ser Thr Asn Phe Val Asp Ala Leu Ile Glu Val Gln Gly Thr Ala
            420                 425                 430

Ile Gln Arg Ile Leu Tyr Cys Asp Asp Pro Val Ser Gln Leu Lys Cys
        435                 440                 445

Ser Gln Val Ala Phe Asp Leu Asp Asp Gly Phe Tyr Pro Ile Ser Ser
    450                 455                 460

Arg Asn Leu Leu Ser His Glu Gln Pro Ile Ser Phe Val Thr Leu Pro
465                 470                 475                 480

Ser Phe Asn Asp His Ser Phe Val Asn Ile Thr Val Ser Ala Ser Phe
                485                 490                 495

Gly Gly His Ser Gly Ala Asn Leu Ile Ala Ser Asp Thr Thr Ile Asn
            500                 505                 510

Gly Phe Ser Ser Phe Cys Val Asp Thr Arg Gln Phe Thr Ile Ser Leu
        515                 520                 525

Phe Tyr Asn Val Thr Asn Ser Tyr Gly Tyr Val Ser Lys Ser Gln Asp
    530                 535                 540

Ser Asn Cys Pro Phe Thr Leu Gln Ser Val Asn Asp Tyr Leu Ser Phe
545                 550                 555                 560

Ser Lys Phe Cys Val Ser Thr Ser Leu Leu Ala Ser Ala Cys Thr Ile
                565                 570                 575

Asp Leu Phe Gly Tyr Pro Glu Phe Gly Ser Gly Val Lys Phe Thr Ser
            580                 585                 590

Leu Tyr Phe Gln Phe Thr Lys Gly Glu Leu Ile Thr Gly Thr Pro Lys
        595                 600                 605

Pro Leu Glu Gly Val Thr Asp Val Ser Phe Met Thr Leu Asp Val Cys
    610                 615                 620

Thr Lys Tyr Thr Ile Tyr Gly Phe Lys Gly Glu Gly Ile Ile Thr Leu
625                 630                 635                 640

Thr Asn Ser Ser Phe Leu Ala Gly Val Tyr Tyr Thr Ser Asp Ser Gly
                645                 650                 655

Gln Leu Leu Ala Phe Lys Asn Val Thr Ser Gly Ala Val Tyr Ser Val
            660                 665                 670

Thr Pro Cys Ser Phe Ser Glu Gln Ala Ala Tyr Val Asp Asp Asp Ile
        675                 680                 685

Val Gly Val Ile Ser Ser Leu Ser Ser Ser Thr Phe Asn Ser Thr Arg
    690                 695                 700

Glu Leu Pro Gly Phe Phe Tyr His Ser Asn Asp Gly Ser His His His
705                 710                 715                 720

His His His His His
                725
```

<210> SEQ ID NO 2
<211> LENGTH: 2178
<212> TYPE: DNA
<213> ORGANISM: porcine epidemic diarrhea virus

<400> SEQUENCE: 2

```
tgctccgcta acaccaactt ccgtcgtttc ttcagcaagt tcaacgtgca ggctcccgct      60

gtggtggtgc tcggtggtta cttgcctatc ggagagaacc agggtgtcaa ctccacctgg     120

tactgcgctg gtcaacaccc tactgcttcc ggtgtccacg gtatcttcgt gtcccacatc     180

cgtggtggtc acggtttcga gatcggtatc tcccaagagc ctttcgaccc ctccggttac     240

cagctgtacc tgcacaaggc taccaacggc aacaccaacg ctaccgctcg tctgaggatc     300
```

-continued tgtcagttcc catccatcaa gaccctgggt cctaccgcta acaacgacgt caccaccggt 360
cgtaactgcc tgttcaacaa ggctatcccc gctcacatgt ccgagcactc cgtcgtgggt 420
atcacctggg acaacgaccg tgtgaccgtg ttctccgaca agatctacta cttctacttc 480
aagaacgact ggtcccgtgt ggctaccaag tgctacaact ccggtggttg cgctatgcag 540
tacgtgtacg agcccaccta ctacatgctg aacgtgacct ctgctggcga ggacggcatc 600
tcttaccagc cttgcaccgc taactgcatc ggttacgctg ctaacgtgtt cgctaccgag 660
cctaacggtc atatccccga gggtttcagc ttcaacaact ggttcctgct gtccaacgac 720
tctaccctgg tgcacggaaa ggtggtgtcc aaccagcctc tgttggtcaa ctgcctgctg 780
gctatcccta agatctacgg cctgggccag ttcttctcat tcaaccagac catcgacggt 840
gtctgcaacg gtgctgctgt gcagcgtgct cctgaagctc tgcgtttcaa catcaacgac 900
acctccgtga tcctggctga gggttccatc gtgctgcaca ccgctctggg tactaacttc 960
tccttcgtgt gctccaactc tagcaaccct cacctggcta ccttcgctat ccctctgggt 1020
gctactcagg tgccctacta ctgtttcttc aaggtggaca cctacaactc gaccgtgtac 1080
aagttcctgg ccgtgctgcc tcctaccgtg cgtgaaatcg tgatcactaa gtacggcgac 1140
gtgtacgtga acggtttcgg ttacctgcac ctgggcctgc tggacgctgt gaccatcaac 1200
ttcaccggtc acggaaccga cgacgacgtg tccggtttct ggactatcgc ttctaccaac 1260
ttcgtggacg ctctgatcga ggtgcagggc actgctatcc agcgtatcct gtactgcgac 1320
gaccccgtgt ctcagctgaa gtgctcccaa gtcgctttcg acctggacga cggtttctac 1380
cccatctcct ctcgtaacct gctgtctcac gagcagccca tcagcttcgt gaccctgcct 1440
tccttcaacg accactcctt cgtcaatatt accgtgtccg cttccttcgg tggtcactcc 1500
ggtgctaacc tgatcgcttc cgacactact atcaacggct tctcctcctt ctgcgtcgac 1560
acccgtcagt tcactatctc cctgttctac aacgtgacca actcctacgg ttacgtgtcc 1620
aagtctcagg actctaactg ccccttcaca ctgcagtccg tgaacgacta cctgagcttc 1680
tccaagttct gcgtgtccac cagtctgctg gcttccgctt gcaccatcga cctgttcggc 1740
taccctgagt tcggttccgg cgtgaagttc acctctctgt acttccagtt caccaagggc 1800
gagctgatca ccggtactcc taagcctctg gaaggtgtca ctgacgtgtc cttcatgacc 1860
ctggacgtgt gcaccaagta caccatctac ggtttcaaag gcgagggcat cattaccctg 1920
actaactcct ctttcctggc tggcgtgtac tacacctccg actctggaca gctgctcgct 1980
ttcaagaatg tgacctccgg cgctgtgtac tccgtgactc cttgcagctt ctccgagcag 2040
gctgcttacg tggacgatga tatcgtgggc gtgatctcca gcctgtcctc ctccaccttc 2100
aactctaccc gtgaactgcc cggtttcttc taccactcca acgacggttc ccaccaccat 2160
catcaccatc accactaa 2178

<210> SEQ ID NO 3
<211> LENGTH: 2253
<212> TYPE: DNA
<213> ORGANISM: Artificial Sequence
<220> FEATURE:
<223> OTHER INFORMATION: PEDV S1 + Signal peptide

<400> SEQUENCE: 3
atgaagtccc tgacctactt ctggctgttc ctgcctgtgc tgtctaccct gtcactgcct 60
caagacgtga cccgttgctc cgctaacacc aacttccgtc gtttcttcag caagttcaac 120
gtgcaggctc ccgctgtggt ggtgctcggt ggttacttgc ctatcggaga gaaccagggt 180

```
gtcaactcca cctggtactg cgctggtcaa caccctactg cttccggtgt ccacggtatc    240

ttcgtgtccc acatccgtgg tggtcacggt ttcgagatcg gtatctccca agagcctttc    300

gacccctccg gttaccagct gtacctgcac aaggctacca acggcaacac caacgctacc    360

gctcgtctga ggatctgtca gttcccatcc atcaagaccc tgggtcctac cgctaacaac    420

gacgtcacca ccggtcgtaa ctgcctgttc aacaaggcta tccccgctca catgtccgag    480

cactccgtcg tgggtatcac ctgggacaac gaccgtgtga ccgtgttctc cgacaagatc    540

tactacttct acttcaagaa cgactggtcc cgtgtggcta ccaagtgcta caactccggt    600

ggttgcgcta tgcagtacgt gtacgagccc acctactaca tgctgaacgt gacctctgct    660

ggcgaggacg gcatctctta ccagccttgc accgctaact gcatcggtta cgctgctaac    720

gtgttcgcta ccgagcctaa cggtcatatc cccgagggtt tcagcttcaa caactggttc    780

ctgctgtcca acgactctac cctggtgcac ggaaaggtgg tgtccaacca gcctctgttg    840

gtcaactgcc tgctggctat ccctaagatc tacggcctgg gccagttctt ctcattcaac    900

cagaccatcg acggtgtctg caacggtgct gctgtgcagc gtgctcctga agctctgcgt    960

ttcaacatca acgacacctc cgtgatcctg gctgagggtt ccatcgtgct gcacaccgct   1020

ctgggtacta acttctcctt cgtgtgctcc aactctagca accctcacct ggctaccttc   1080

gctatccctc tgggtgctac tcaggtgccc tactactgtt tcttcaaggt ggacacctac   1140

aactcgaccg tgtacaagtt cctggccgtg ctgcctccta ccgtgcgtga aatcgtgatc   1200

actaagtacg gcgacgtgta cgtgaacggt ttcggttacc tgcacctggg cctgctggac   1260

gctgtgacca tcaacttcac cggtcacgga accgacgacg acgtgtccgg tttctggact   1320

atcgcttcta ccaacttcgt ggacgctctg atcgaggtgc agggcactgc tatccagcgt   1380

atcctgtact gcgacgaccc cgtgtctcag ctgaagtgct cccaagtcgc tttcgacctg   1440

gacgacggtt tctaccccat ctcctctcgt aacctgctgt ctcacgagca gcccatcagc   1500

ttcgtgaccc tgccttcctt caacgaccac tccttcgtca atattaccgt gtccgcttcc   1560

ttcggtggtc actccggtgc taacctgatc gcttccgaca ctactatcaa cggcttctcc   1620

tccttctgcg tcgacacccg tcagttcact atctccctgt tctacaacgt gaccaactcc   1680

tacggttacg tgtccaagtc tcaggactct aactgcccct tcacactgca gtccgtgaac   1740

gactacctga gcttctccaa gttctgcgtg tccaccagtc tgctggcttc cgcttgcacc   1800

atcgacctgt tcggctaccc tgagttcggt tccggcgtga agttcacctc tctgtacttc   1860

cagttcacca agggcgagct gatcaccggt actcctaagc ctctggaagg tgtcactgac   1920

gtgtccttca tgaccctgga cgtgtgcacc aagtacacca tctacggttt caaaggcgag   1980

ggcatcatta ccctgactaa ctcctctttc ctggctggcg tgtactacac ctccgactct   2040

ggacagctgc tcgctttcaa gaatgtgacc tccggcgctg tgtactccgt gactccttgc   2100

agcttctccg agcaggctgc ttacgtggac gatgatatcg tgggcgtgat ctccagcctg   2160

tcctcctcca ccttcaactc tacccgtgaa ctgcccggtt tcttctacca ctccaacgac   2220

ggttcccacc accatcatca ccatcaccac taa                                2253
```

<210> SEQ ID NO 4
<211> LENGTH: 28063
<212> TYPE: DNA
<213> ORGANISM: porcine epidemic diarrhea virus

<400> SEQUENCE: 4

```
acttaaagag attttctatc tacggatagt tagctctttt tctagactct tgtctactca     60
attcaactaa acgaaatttt gtccttccgg ccgcatgttc atgctgctgg aagtcgacgt    120
ggaatttcat taggtttgct taagtagcca tcgcaagtgc tgtgctgtcc tctagttcct    180
ggttggcgtt ccgtcgcctt ctacatacta gacaaacagc cttcctccgg ttccgtctgg    240
gggttgtgtg gataactagt tccgtctagt ttgaaaccag taactgccgg ctatggctag    300
caaccatgtc acattggcat ttgccaatga tgcagaaatt tcagcttttg gcttttgcac    360
tgctagtgaa gccgtctcat actattctga ggccgcctct agtggattta tgcaatgccg    420
tttcgtgtcc ttcgatctcg ctgacattgt tgagggattg cttcccgaag actatgtcat    480
ggtggtggtc ggcactacca agcttagtgc gtatgtggat acttttaata gccgccccag    540
aaacatttgt ggttggctgt tattttctaa ctgtaattac ttccttgaag atttagagct    600
cacttttggt cgtcgtggtg gtaacatcgt gccagttgac caatacatgt gtggcgctga    660
cggtaaacct gttcttcagg aatccgaatg ggagtataca gatttctttg ctgactccga    720
agacggtcaa ctcaacattg ctggtatcac ttatgtgaag gcctggattg tagagcgatc    780
ggatgtctct tatgcgagtc agaatttaac atctattaag tctattactt actgttcaac    840
ctatgagcat acttttcctg atggtactgc catgaaggtt gcacgtactc caaagattaa    900
gaagactgtt gtcttgtctg agccacttgc tactatctac agggaaattg gttctccttt    960
tgtggataat gggagcgatg ctcgttctat cattaagaga ccagtgttcc tccacgcttt   1020
tgttaagtgt aagtgtggta gttatcattg gactgttggt gattggactt cctatgtctc   1080
cacttgctgt ggctttaatt gtaagccagt ccttgtggct tcatgctctg ctacgcctgg   1140
ttctgttgtg gttacgcgcg ctggtgctgg cactggtgtt aagtattaca acaacatgtt   1200
cctgcgccat gtggcagaca ttgatgggtt ggcattctgg cgaattctca aggtgcagtc   1260
caaagacgac ctcgcttgct ctggtaaatt ccttgaacac catgaggaag gtttcacaga   1320
tccttgctac tttttgaatg actcgagcat tgctactaag ctcaagtttg acatccttag   1380
tggcaagttt tctgatgaag tcaaacaagc tatctttgct ggtcatgttg ttgttggcag   1440
cgcgctcgtt gacattgttg atgatgcact gggacagcct tggtttatac gtaagcttgg   1500
tgaccttgca agtgcagctt gggagcagct taaggctgtc gttagaggcc ttaacctcct   1560
ggctgatgag gtcgtgctct ttggcaaaag acttagctgt gccactctta gtatcgttaa   1620
cggtgttttt gagttcatcg ccgaagtgcc tgagaagttg gctgcggctg ttacagtttt   1680
tgtcaacttc ttgaatgagc tttttgagtc tgcctgtgac tgcttaaagg tcggaggtaa   1740
aacctttaac aaggttggct cttatgttct ttttgacaac gcattggtta agcttgtcaa   1800
ggcaaaagtt cgcggcccac gacaggcagg tgtttgtgaa gttcgttaca caagccttgt   1860
tattgggagt actaccaagg tggtttccaa gcgcgttgaa aatgccaatg tgaatctcgt   1920
cgtcgttgac gaggatgtga ccctcaacac cactggtcgt acagttgttg ttgacggact   1980
tgcattcttc gagagtgacg ggttttacag acatcttgct gatgctgacg ttgtcattga   2040
acatcctgtt tataagtctg cttgtgagct caagccagtt tttgagtgtg acccaatacc   2100
tgattttcct atgcctgtgg ccgctagtgt tgcagagctt tgtgtgcaaa ttgatctgtt   2160
gcttaaaaat tacaacactc cttataaaac ttacagctgc gttgtgagag gtgataagtg   2220
ttgcatcact tgcaccttac atatcacagc accaagttat atggaggatg ctgctaattt   2280
```

-continued

```
tgtagacctc tgtaccaaga acattggtac tgctggtttt catgagtttt acattacggc   2340
ccatgaacaa caggatctgc aagggttcgt aaccacttgt tgcacgatgt caggttttga   2400
gtgttttatg cctataatcc cacagtgtcc agcagtgctt gaagagattg atggtggtag   2460
catctggcgg tcttttatca ctggtattaa tacaatgtgg gatttttgca agcatcttaa   2520
agtcagcttt ggactagatg gcattgttgt cactgtagca cgcaaattta aacgacttgg   2580
tgctctcttg gcagaaatgt ataacactta ccttttaact gtggtggaaa acttggtact   2640
ggccggtgtt agcttcaagt attatgccac cagtgtccca aaaattgttt tgggctgttg   2700
ttttcacagt gttaaaagtg ttcttgcaag tgccttccag attcctgtcc aggcaggcat   2760
tgagaagttt aaagtcttcc ttaactgtgt tcaccctgtt gtaccacgcg tcattgaaac   2820
ttcttttgtg gaattagaag agacgacatt taaaccacca gcactcaatg gtagtattgc   2880
tattgttgat ggctttgctt tctattatga tggaacacta tactatccca ccgatggtaa   2940
tagtgttgtg cctatttgtt ttaagaagaa gggtggtggt gatgtcaaat tctctgatga   3000
agtctctgtt agaaccattg acccagttta taaggtctcc cttgaatttg agttcgagtc   3060
tgagactatt atggctgtgc ttaataaggc tgttggtaat cgtatcaagg ttacaggtgg   3120
ttgggacgat gttgttgagt atatcaacgt tgccattgag gttcttaaag accatatcga   3180
tgtgcctaag tactacatct atgatgagga aggtggcacc gatcctaatc ttcccgtaat   3240
ggtttctcag tggccgttga atgatgacac gatctcacag gatctgcttg atgtggaagt   3300
tgttactgat gcaccaattg atttcgaggg tgatgaagta gactcctctg accctgataa   3360
ggtgtcagat gtggctaact ctgagcctga ggatgatggt cctaatgtag ctcctgaaac   3420
aaatgtagag tctgaagttg aggaagttgc cgcaaccttg ttttttatta aagatacacc   3480
ttccacagtt actaaggatc cttttgcttt tgactttgca agctatggag gacttaaggt   3540
tttaagacaa tctcataaca actgctgggt tacttctacc ttggtgcagc tacaattgct   3600
tggcatcgtt gatgaccctg caatggagct ttttagtgct ggtagagttg gtccaatggt   3660
tcgcaaatgc tatgagtcac aaaaggctat cttgggatct ttgggtgatg tgtcggcttg   3720
cctagagtct ctgactaagg acctacacac acttaagatt acctgttctg tagtctgtgg   3780
ttgtggtact ggtgaacgta tctatgaggg ttgtgctttt cgtatgacgc caactttgga   3840
accgttccca tatggtgctt gtgctcagtg tgctcaagtt ttgatgcaca cttttaaaag   3900
tattgttggc accggcatct tttgtcgaga tactactgct ctctccttgg attctttggt   3960
tgtaaaacct ctttgtgcgg ctgcttttat aggcaaggac agtggtcatt atgtcactaa   4020
cttttatgat gctgctatgg ctattgatgg ttatggtcgt catcagataa agtatgacac   4080
actgaacact atttgtgtta aagacgttaa ttggacagca ccttttgtcc cagacgttga   4140
gcctgtattg gagcctgttg tcaaaccgtt ctattcttat aagaatgttg atttttacca   4200
aggagatttt agtgaccttg ttaaacttcc atgtgacttt gttgttaatg ctgcaaatga   4260
gaatttgtct cacggtggcg gcatagcaaa ggccattgat gtttatacca agggcatgtt   4320
gcagaagtgc tcgaatgatt acattaaagc acacggtccc attaaagttg gacgtggtgt   4380
catgttggag gcattaggtc ttaaggtctt taatgttgtt ggtccacgta agggtaagca   4440
tgcacctgag cttcttgtta aggcttataa gtccgttttt gctaattcag gtgttgctct   4500
tacacctttg attagtgttg gaatttttag tgttcctttg gaagaatctt tatctgcttt   4560
tcttgcatgt gttggtgatc gccactgtaa gtgcttttgt tatagtgaca aagagcgcga   4620
ggcgatcatt aattacatgg atggcttggt agatgctatt ttcaaagatg cacttgttga   4680
```

```
tactactcct atccaggaag atgttcaaca agtttcacaa aaaccagttt tgcctaattt   4740
tgaacctttc aggattgaag gtgctcatgc tttctatgag tgcaaccctg aaggtttgat   4800
gtcattaggt gctgacaagc tggtgttgtt tacaaattcc aatttggatt tttgtagcgt   4860
tggtaagtgt cttaacaatg tgactggcgg tgcattgctt gaagccataa atgtatttaa   4920
aaagagtaac aaaacagtgc ctgctggcaa ctgtgttact tttgagtgtg cagatatgat   4980
ttctattact atggtagtat tgccatctga cggtgatgct aattatgaca aaaattatgc   5040
acgcgccgtc gtcaaggtat ctaagcttaa aggcaagtta ttgcttgctg ttggtgatgc   5100
catgttgtat tccaagttgt cccacctcag cgtgttaggt ttcgtatcca cacctgatga   5160
tgtggagcgt ttctacgcaa ataagagtgt ggttattaaa gttactgagg atacacgtag   5220
tgttaagact gttaaagtag aatccactgt tacttatgga caacaaattg gaccttgtct   5280
tgttaatgac accgttgtca cagacaacaa acctgttgtt gctgatgttg tagctaaggt   5340
tgtaccaagt gctaattggg attcacatta tggttttgat aaggctggtg agttccacat   5400
gctagaccat actgggtttg cctttcctag tgaagttgtt aacggtaggc gtgtgcttaa   5460
aaccacagat aataactgtt gggttaatgt tacatgttta caattacagt ttgctagatt   5520
taggttcaag tcagcaggtc tacaggctat gtgggagtcc tattgtactg gtgatgttgc   5580
tatgtttgtg cattggttgt actggcttac tggtgttgac aaaggtcagc ctagtgattc   5640
agaaaatgca cttaacatgt tgtctaagta cattgttcct gctggttctg tcactattga   5700
acgtgtcacg catgacggtt gttgttgtag taagcgtgtt gtcactgcac cagttgtgaa   5760
tgctagcgtg ttgaagcttg gcgtcgagga tggtctttgt ccacatggtc ttaactacat   5820
tgacaaagtt gttgtagtta aaggtactac aattgttgtc aatgttggaa aacctgtagt   5880
ggcaccatcg cacctctttc ttaagggtgt ttcctacaca acattcctag ataatggtaa   5940
cggtgttgcc ggccattata ctgtttttga tcatgacact ggtatggtgc atgatggaga   6000
tgtttttgta ccaggtgatc tcaatgtgtc tcctgttaca aatgttgtcg tctcagagca   6060
gacggctgtt gtgattaaag accctgtgaa gaaagtagag ttagacgcta caaagctgtt   6120
agacactatg aattatgcat cggaaagatt cttttccttt ggtgatttta tgtcacgtaa   6180
tttaattaca gtgtttttgt acatccttag tattttgggt ctctgtttta gggcctttcg   6240
taagagggat gttaaagttc tagctggtgt accccaacgt actggtatta tattgcgtaa   6300
aagtgtgcgc tataatgcaa aggctttggg tgtcttcttc aagctaaaac tttattggtt   6360
caaagttctt ggtaagttta gtttgggtat ttatgcattg tatgcattac tattcatgac   6420
aatacgcttt acacctatag gtggccctgt ttgtgatgat gttgttgctg gttatgctaa   6480
ttctagtttt gacaagaatg agtattgcaa cagtgttatt tgtaaggtct gtctctatgg   6540
gtaccaggaa ctttcggact tctctcacac acaggtagta tggcaacacc ttagagaccc   6600
attaattggt aatgtgatgc ctttctttta tttggcattt ctggcaattt ttggggggtgt   6660
ttatgtaaag gctattactc tctattttat tttccattat cttaacatac ttggtgtgtt   6720
tttgggccta caacagtcca tttggttttt gcagcttgtg ccttttgatg tctttggtga   6780
cgagatcgtc gtctttttca tcgttacacg cgtattgatg ttccttaagc atgttttcct   6840
tggctgcgat aaggcatctt gtgtggcttg ctctaagagt gctcgcctta agcgcgttcc   6900
tgtccagact atttttcagg gtactagcaa atccttctac gtacatgcca atggtggttc   6960
taagttctgt aagaagcaca atttcttttg tttaaattgt gattcttatg gtccaggctg   7020
```

```
cacttttatt aatgacgtca ttgcaactga agttggtaat gttgtcaaac ttaatgtgca   7080
accgacaggt cctgccacta ttcttattga caaggttgaa ttcagtaatg gtttttacta   7140
tctttatagt ggtgacacat tttggaagta caactttgac ataacagata acaaatacac   7200
ttgcaaagag tcacttaaaa attgtagcat aatcacagac tttattgttt ttaacaataa   7260
tggttccaat gtaaatcagg ttaagaatgc atgtgtgtat ttttcacaga tgctttgtaa   7320
acctgttaag ttagtggact cagcgttgtt ggccagtttg tctgttgatt ttggtgcaag   7380
cttacatagt gcttttgtta gtgtgttgtc gaatagtttt ggcaaagacc tgtcaagttg   7440
taatgacatg caggattgca agagcacatt gggttttgat gatgtaccat tggatacctt   7500
taatgctgct gttgctgagg ctcatcgtta cgatgtcctc ttgactgaca tgtcgttcaa   7560
caatttacc accagttatg caaaaccaga ggaaaaactt cccgtccatg acattgccac   7620
gtgtatgcgt gtaggtgcca agattgttaa tcataacgtt cttgtcaagg atagtatacc   7680
tgtggtgtgg cttgtacgtg atttcattgc cctttctgaa gaaactagga agtacattat   7740
tcgtacgact aaagttaagg gtataacctt catgttgacc tttaatgatt gtcgtatgca   7800
tactaccata cctactgttt gcattgcaaa taagaagggt gcaggtcttc ctagtttttc   7860
aaaggttaag aaattcttct ggtttttgtg tctgttcata gttgctgttt tctttgcact   7920
aagcttttt gattttagta ctcaggttag cagtgatagt gattatgact tcaagtatat   7980
tgagagtggc cagttgaaga cttttgacaa tccacttagt tgtgtgcata atgtctttag   8040
taacttcgac cagtggcatg atgccaagtt tggtttcacc cccgtcaaca atcctagttg   8100
tcctatagtc gttggtgtat cagacgaagc gcgcactgtt ccaggtatcc cagcaggtgt   8160
ttatttagct ggtaaaacac ttgtttttgc tattaacacc atttttggta catctggttt   8220
gtgctttgat gctagtggcg ttgctgataa gggcgcttgc atttttaatt cggcttgcac   8280
cacattatct ggtttgggtg gaactgctgt ctactgttat aagaatggtc tagttgaagg   8340
tgctaaactt tatagtgagt tggcacctca tagctactat aaaatggtag atggtaatgc   8400
tgtgtcttta cctgaaatta tctcacgcgg ctttggcatc cgtactatcc gtacaaaggc   8460
tatgacctac tgtcgcgttg gccagtgtgt gcaatctgca gaaggtgttt gttttggcgc   8520
cgatagattc tttgtctata atgcagaatc tggttctgac tttgtttgtg gcacagggct   8580
ctttacattg ttgatgaacg ttattagtgt tttttccaag acagtaccag taactgtgtt   8640
gtctggtcaa atacttttta attgcattat tgcttttgct gctgttgcgg tgtgtttctt   8700
atttacaaag tttaagcgca tgttcggtga tatgtctgtt ggcgttttca ctgtcggtgc   8760
ttgtactttg ttgaacaatg tttcctacat tgtaacacag aacacacttg gcatgttggg   8820
ctatgcaact ttgtactttt tgtgcactaa aggtgttaga tatatgtgga tttggcattt   8880
gggatttttg atctcatata tacttattgc accatggtgg gttttgatgg tttatgcctt   8940
ttcagccatt tttgagttta tgcctaacct ttttaagctt aaggtttcaa cacaactttt   9000
tgagggtgac aagttcgtag gctcttttga aaatgctgca gcaggtacat ttgtgcttga   9060
tatgcatgcc tatgagagac ttgccaactc tatctcaact gcaaaactgc gtcagtatgc   9120
tagtacttac aataagtaca agtattattc aggcagtgct tcagaggctg attacaggct   9180
tgcttgtttt gcccatttgg ccaaggctat gatggattat gcttctaatc acaacgacac   9240
gttatacaca ccacccactg tgagttacaa ttcaactcta caggctggct tgcgtaagat   9300
ggcacaacca tctggtgttg ttgagaagtg catagttcgt gtttgctatg gtaatatggc   9360
tcttaatggc ctatggcttg gtgatactgt tatctgccca cgccatgtta tagcgtctag   9420
```

-continued

```
tactactagc actatagatt atgactatgc cctttctgtt ttacgcctcc acaacttctc   9480
catttcatct ggtaatgttt tcctaggtgt tgtgggtgta accatgcgag gtgctttgtt   9540
gcagataaag gttaatcaaa acaatgtcca cacgcctaag tacacctatc gcacagttag   9600
accgggtgaa tcttttaata tcttggcgtg ctatgatggt tctgcagctg gtgtttacgg   9660
cgttaacatg cgctctaatt acactattag aggctcgttc attaatggcg cttgtggttc   9720
acctggttat aacattaaca atggtaccgt tgagttttgc tatttacacc agcttgaact   9780
tggttcaggc tgtcatgttg gtagcgactt agatggtgtt atgtatggtg gttatgagga   9840
ccaacctact ttgcaagttg aaggcgctag tagtctgttt acagagaatg tgttggcatt   9900
tctttatgca gcactcatta atggttctac ctggtggctt agttcttcta ggattgctgt   9960
agacaggttt aatgagtggg ctgttcataa tggtatgaca acagtagtta atactgattg  10020
cttttctatt cttgctgcta agactggtgt tgatgtacaa cgtttgttgg cctcaatcca  10080
gtctctgcat aagaattttg gtggaaagca aattcttggc tatacctcgt tgacagatga  10140
gtttactaca ggtgaagtca tacgtcaaat gtatggcgtt aatcttcaga gtggttatgt  10200
ttcacgcgcc tgtagaaatg tcttgctggt tggttctttt ctgactttct tttggtcaga  10260
attagtttcc tacactaagt tcttttgggt aaatcctggt tatgtcacac ctatgtttgc  10320
gtgtttgtca ttgctgtcct cacttttgat gttcacacgg agcataagac attgtttttc  10380
caggtctttc taatacctgc tctgattgtt acatcttgca ttaatttggc atttgatgtt  10440
gaagtctaca actatttggc agagcatttt gattaccatg tttctctcat gggttttaat  10500
gcacaaggtc ttgttaacat ctttgtctgc tttgttgtta ccattttaca cggcacatac  10560
acatggcgct tttttaacac acctgtgagt tctgtcactt atgtggtagc tttgctgact  10620
gcggcatata actattttta cgctagtgac attcttagtt gtgctatgac actatttgct  10680
agtgtgactg gcaactggtt cgttggtgct gtttgttata aagctgctgt ttatatggcc  10740
ttgagatttc ctacttttgt ggctattttt ggtgatatta agagtgttat gttctgttac  10800
cttgtgttgg gttattttac ctgttgcttc tacggtattc tctactggtt caacaggttt  10860
tttaaggtta gtgtaggtgt ctatgactat actgttagtg ctgctgagtt taagtatatg  10920
gttgctaacg gcctacgtgc accaactgga acacttgatt cactacttct gtctgccaaa  10980
ttgattggta ttggtggtga gcggaatatt aagatttctt ccgttcagtc taaactgact  11040
gatattaagt gtagtaacgt tgtgctttta ggctgtctct ctagcatgaa tgtctcagca  11100
aattcaacag aatgggccta ttgtgttgac ttgcataaca agatcaactt gtgtaatgac  11160
ccagaaaaag cgcaggaaat gctacttgct ttgttggcat tttccttag taagaatagt  11220
gcttttggtt tagatgactt attggaatcc tattttaatg acaatagtat gttgcagagt  11280
gttgcatcta cttatgtcgg tttgccttct tatgtcattt atgaaaatgc acgccaacag  11340
tatgaagatg ctgttaataa tggttctcca cctcagttgg ttaagcaatt gcgccatgcc  11400
atgaatgtag caaagagcga atttgaccgt gaggcttcta ctcagcgtaa gcttgataga  11460
atggcggaac aggctgcagc acagatgtac aaagaggcac gagcagttaa taggaagtcc  11520
aaagttgtaa gtgctatgca ttcactgctt tttggtatgt tgagacgttt ggacatgtct  11580
tctgtagaca ccattctcaa cttggcaaag gatggggttg tacctctgtc tgtcataccg  11640
gcagtcagtg ctactaagct taacattgtt acttctgata tcgattctta taatcgtatc  11700
cagcgtgagg gatgtgtcca ctacgctggt accatttgga atataattga tatcaaggac  11760
```

-continued

```
aatgatggca aggtggtaca cgttaaggag gtaaccgcac agaatgctga gtccctgtca  11820
tggcccctgg tccttgggtg tgagcgtatt gtcaagctcc agaataatga aattattcct  11880
ggtaagctga agcagcgctc cattaaggca gaaggagatg gcatagttgg agaaggtaag  11940
gcactttata ataatgaggg tggacgtact tttatgtatg ctttcatctc ggacaaaccg  12000
gacctgcgtg tagtcaagtg ggagttcgat ggtggttgta acactattga gctagaacca  12060
ccacgtaagt tcttggtgga ttctcctaat ggtgcacaga tcaagtatct ctactttgtt  12120
cgtaacctta acacgttacg taggggtgct gttctcggct acataggtgc cactgtacgc  12180
ttgcaggctg gtaaacaaac agaacaggct attaactctt cattgttgac actttgcgct  12240
ttcgctgtgg atcctgctaa gacctacatc gatgctgtca aaagtggtca caaaccagta  12300
ggtaactgtg ttaagatgtt ggccaatggt tctggtaatg gacaagctgt tactaatggt  12360
gtagaggcta gtactaacca ggattcatac ggtggtgcgt ccgtgtgtct atattgtaga  12420
gcacatgttg agcatccatc tatggatggt tttgcagac  tgaaaggcaa gtacgtacag  12480
gttccactag gtacagtgga tcctatacgt tttgtacttg agaatgacgt ttgcaaggtt  12540
tgtggttgtt ggctggctaa tggctgcact tgtgacagat ccattatgca aagcactgat  12600
atggcttatt taaacgagta cggggctcta gtgcagctcg actagagccc tgtaacggta  12660
ctgatacaca acatgtgtat cgtgcttttg acatctacaa caaggatgtt gcttgtctag  12720
gtaaattcct caaggtgaac tgtgttcgcc tgaagaattt ggataagcat gatgcattct  12780
atgttgtcaa aagatgtacc aagtctgcga tggaacacga gcaatccatc tatagcagac  12840
ttgaaaagtg tggagccgta gccgaacacg atttcttcac ttggaaggat ggtcgtgcca  12900
tctatggtaa cgtttgtaga aaggatctta ccgagtatac tatgatggat ttgtgttacg  12960
ctttacgtaa ctttgatgaa aacaattgcg atgttcttaa gagcatttta attaaggtag  13020
gcgcttgtga ggagtcctac ttcaataata aagtctggtt tgaccctgtt gaaaatgaag  13080
acattcatcg tgtctatgca ttgttaggta ccattgtttc acgtgctatg cttaaatgcg  13140
ttaagttctg tgatgcaatg gttgaacaag gtatagttgg tgttgtcaca ttagataatc  13200
aggatcttaa tggtgatttt tatgattttg gtgattttac ttgtagcatc aagggaatgg  13260
gtatacccat ttgcacatca tattactctt atatgatgcc tgttatgggt atgactaatt  13320
gccttgctag tgagtgtttt gttaagagtg atatatttgg tgaggatttc aagtcatatg  13380
acctgctgga atatgatttc acggagcata agacagcact cttcaacaag tatttcaagt  13440
attggggact gcaataccac cctaactgtg tggactgcag tgatgagcag tgcatagttc  13500
actgtgccaa cttcaatacg ttgttttcca ctactatacc tattacggca tttggacctt  13560
tgtgtcgcaa gtgttggatt gatggtgttc cactggtaac tacagctggt tatcatttta  13620
aacagttagg tatagtttgg aacaatgacc tcaacttaca ctctagcagg ctctctatta  13680
acgaattact ccagttttgt agtgatcctg cattgcttat agcatcatca ccagcccttg  13740
ttgatcagcg tactgtttgc ttttcagttg cagcgctagg tacaggtatg actaaccaga  13800
ctgttaaacc tggccatttc aataaggagt tttatgactt cttacttgag caaggtttct  13860
tttctgaggg ctctgagctt actttaaagc acttcttctt tgcacagaag ggtgatgcag  13920
ctgttaagga ttttgactac tataggtata atagacctac tgttctggac atttgccaag  13980
ctcgcgtcgt gtatcaaata gtgcaacgct attttgatat ttacgaaggt ggttgtatca  14040
ctgctaaaga ggtggttgtt acaaacctta acaagagcgc aggttatcct ttgaacaagt  14100
ttggtaaagc tggtctttac tatgagtctt tatcctatga ggaacaggat gaactttatg  14160
```

```
cttatactaa gcgtaacatc ctgcccacta tgacacagct caaccttaaa tatgctataa  14220
gtggcaaaga acgtgcacgc acagtgggtg gtgtttcgct tttgtcaacc atgactactc  14280
ggcagtatca tcagaaacac cttaagtcca tagttaatac taggggcgct tcggttgtta  14340
ttggtactac taagttttat ggtggttggg acaatatgct taagaacctt attgatggtg  14400
ttgaaaatcc gtgtcttatg ggttgggact acccaaagtg cgacagagca ctgcccaata  14460
tgatacgtat gatttcagcc atgattttag gctctaagca caccacatgc tgcagttcca  14520
ctgaccgctt tttcaggttg tgcaatgaat tggctcaagt ccttactgag gttgtttatt  14580
ctaatggagg tttttatttg aagccaggtg gtactacctc tggtgatgca accaccgcat  14640
atgcaaactc agtttttaat atcttccaag cagtaagtgc caatgttaac aaacttctta  14700
gtgttgacag caatgtctgt cataatttag aagttaagca attgcagcgt aagctttatg  14760
agtgctgtta tagatcaact accgtcgatg accagttcgt cgttgagtat tatggttact  14820
tgcgtaaaca tttttcaatg atgattcttt ctgatgatgg cgttgtttgt tataacaatg  14880
actatgcatc acttggttat gtcgctgatc ttaacgcatt caaggctgtt ttgtattacc  14940
agaacaatgt cttcatgagc gcctctaaat gttggatcga gcctgacatt aataaaggtc  15000
ctcatgaatt ttgctcgcag catactatgc agattgtcga taaagatggt acttattacc  15060
ttccttaccc tgatccttca agaattctct ctgcaggtgt gtttgttgat gacgttgtta  15120
aaactgatgc agttgtattg cttgaacgtt atgtgtcatt ggctatagat gcctacccgt  15180
tatctaagca tgaaaaccct gaatataaga aggtgtttta tgtgcttttg gattgggtta  15240
agcatctgta caaaactctt aatgctggtg tgttagagtc tttttctgtc acacttttgg  15300
aagattctac tgctaaattc tgggatgaga gcttttatgc caacatgtat gagaaatctg  15360
cagttttaca atctgcaggg ctttgtgttg tttgtggctc tcaaactgtt ttacgttgtg  15420
gtgattgtct acggcgtcct atgctttgta ctaagtgtgc ttatgatcat gtcattggaa  15480
caactcacaa gttcattttg gccatcactc catatgtgtg ttgtgcttca gattgtggtg  15540
tcaatgatgt aactaagctc tacttaggtg gtcttagtta ttggtgtcat gaccacaagc  15600
cacgtcttgc attcccgttg tgctctgctg gtaatgtttt tggcttgtac aaaaattctg  15660
ctaccggctc acccgatgtt gaagacttta atcgcattgc tacatccgat tggactgatg  15720
tttctgacta caggttggca aatgatgtca aggactcatt gcgtctgttt gcagcggaaa  15780
ctatcaaggc caaggaggag agcgttaagt catcctatgc ttgtgcaaca ctacatgagg  15840
ttgtaggacc taaagagttg ttgctcaaat gggaagtcgg cagacccaaa ccacccctta  15900
atagaaattc ggttttcact tgttatcata taacgaagaa caccaaattt caaatcggtg  15960
agtttgtgtt tgagaaggca gaatatgata atgatgctgt aacatataaa actaccgcca  16020
caacaaaact tgttcctggc atggtttttg tgcttacctc acataatgtt cagccattgc  16080
gcgcaccgac cattgctaat caagaacgtt attccactat acataagttg catcctgctt  16140
ttaacatacc tgaagcttat tctagcttag tgccctatta ccaattgatt ggtaagcaga  16200
agattacaac tattcaggga cctcccggta gtggtaaatc tcactgtgtt atagggctag  16260
gtttgtacta tccaggtgca cgtatagtgt ttacagcttg ttctcatgca gcggtcgatt  16320
cactttgtgt gaaagcttcc actgcttata gcaatgacaa atgttcacgc atcataccac  16380
agcgcgctcg tgttgagtgt tatgatggtt tcaagtctaa taatactagt gctcagtacc  16440
ttttctctac tgtcaatgct ttgccagagt gcaatgcgga cattgttgtg gtggatgagg  16500
```

```
tctctatgtg cactaattat gacttgtctg tcataaatca gcgcatcagc tataggcatg  16560
tagtctatgt tggtgaccct caacagctgc ctgcaccacg tgttatgatt tcacgtggta  16620
ctttggaacc aaaggactac aacgttgtca ctcaacgcat gtgtgccctt aagcctgatg  16680
ttttcttgca caagtgttat cgttgtcctg ctgagatagt gcgtactgtg tctgagatgg  16740
tctatgaaaa ccaattcatt cctgtgcacc cagatagcaa gcagtgtttt aaaatctttt  16800
gcaagggtaa tgttcaggtt gataatggtt caagcattaa tcgcaggcaa ttggatgttg  16860
tgcgtatgtt tttggctaaa aatcctaggt ggtcaaaggc tgtttttatt tctccttata  16920
acagccagaa ttatgttgcc agccgcatgc taggtctaca aattcagaca gttgactcat  16980
cccagggtag tgagtatgac tatgtcattt acacacaaac ttcagatact gcccatgcct  17040
gtaatgttaa caggtttaat gtagccatca caagggccaa gaaaggcata ttatgtataa  17100
tgtgcgatag gtcccttttt gatgtgctta aattctttga gcttaaattg tctgatttgc  17160
aggctaatga gggttgtggt ctttttaaag actgtagcag aggtgatgat ctgttgccac  17220
catctcacgc taacaccttc atgtctttag cggacaattt taagactgat caagatcttg  17280
ctgttcaaat aggtgttaat ggacccatta aatatgagca tgttatctcg tttatgggtt  17340
tccgttttga tatcaacata cccaaccatc atactctctt ttgcacacgc gactttgcca  17400
tgcgcaatgt tagaggttgg ttaggctttg acgttgaagg agcacatgtt gttggctcta  17460
acgtcggtac aaatgtccca ttgcaattag ggttttctaa cggtgttgat tttgttgtca  17520
gacctgaagg ttgcgttgta acagagtctg gtgactacat taaacccgtc agagctcgtg  17580
ctccaccagg ggaacaattc gcacaccttt tgcctttact taaacgcggc caaccatggg  17640
atgttgtccg caaacgtata gtgcagatgt gtagtgacta cctggccaac ctatcagaca  17700
tactaatttt tgtgttgtgg gctggtggtt tggagttgac aactatgcgt tattttgtca  17760
agattggacc aagtaagagt tgtgattgtg gtaaggttgc tacttgttac aatagtgcgc  17820
tgcatacgta ctgttgtttc aaacatgccc ttggttgtga ttatctgtat aacccatact  17880
gtattgatat acagcagtgg ggatacaagg gatcacttag ccttaaccac catgagcatt  17940
gtaatgtaca tagaaacgag catgtggctt ctggtgatgc cataatgact cgctgtctgg  18000
ccatacatga ttgctttgtc aagaacgttg actggtccat cacataccca tttattggta  18060
atgaggctgt tattaataag agcggccgaa ttgtgcaatc acacactatg cggtcagttc  18120
ttaagttata caatccgaaa gccatatatg atattggcaa tcctaagggc attagatgtg  18180
ccgtaacgga tgctaaatgg ttttgctttg acaagaatcc tactaattct aatgtcaaga  18240
cattggagta tgactatata acacatggcc aatttgatgg gttgtgcttg ttttggaatt  18300
gcaatgtaga catgtatcca gaattttctg tggtctgtcg ttttgatact cgctgtaggt  18360
caccactcaa cttggagggt tgtaatggtg gttcactgta tgttaataat catgcattcc  18420
atacaccggc ttttgacaag cgtgcttttg ctaagttgaa gccaatgcca tttttctttt  18480
atgatgatac tgagtgtgac aagttacagg actccataaa ctatgttcct cttagggcta  18540
gtaactgcat tactaaatgt aatgttggtg gtgctgtctg tagtaagcat tgtgctatgt  18600
atcatagcta tgttaatgct tacaacactt ttacgtcggc gggctttact atttgggtgc  18660
ctacttcgtt tgacacctat aatctgtggc agacatttag taacaatttg caaggtcttg  18720
agaacattgc tttcaatgtc gtaaagaaag gatcttttgt tggtgccgaa ggtgaacttc  18780
ctgtagctgt ggttaatgac aaagtgctcg ttagagatgg tactgttgat actcttgttt  18840
ttacaaacaa gacatcacta cccactaacg tagcttttga gttgtatgcc aagcgtaagg  18900
```

```
taggactcac cccacccatt acgatcctac gtaacttggg tgtagtttgt acatctaagt  18960
gtgtcatttg ggactatgaa gccgaacgtc cacttactac ttttacaaag gatgtttgta  19020
aatataccga ctttgagggt gacgtctgta cactctttga taacagcatt gttggttcat  19080
tagagcgatt ctccatgacc caaaatgctg tgcttatgtc acttacagct gttaaaaagc  19140
ttactggcat aaagttaact tatggttatc ttaatggtgt cccagttaac acacatgaag  19200
ataaaccttt tacttggtat atttacacta ggaagaacgg caagttcgag gaccatcctg  19260
atggctattt tacccaaggt agaacaaccg ctgattttag ccctcgtagc gacatggaaa  19320
aggacttcct aagtatggat atgggtctgt ttattaacaa gtacggactt gaagattacg  19380
gctttgagca cgttgtgtat ggtgatgttt caaaaaccac ccttggtggt ttgcatctac  19440
taatttcgca ggtgcgtctg gcctgtattg gtgtgctcaa aatagacgag tttgtgtcta  19500
gtaatgatag cacgttaaag tcttgtactg ttacatatgc tgataaccct agtagtaaga  19560
tggtttgtac gtatatggat ctcctgcttg acgattttgt cagcattctt aaatctttgg  19620
atttgggcgt tgtatctaaa gttcatgaag ttatggtcga ttgtaaaatg tggaggtgga  19680
tgttgtggtg taaggatcat aaactccaga cattttatcc gcaacttcag gccagtgaat  19740
ggaagtgtgg ttattccatg ccttctattt acaagataca acgtatgtgt ttagaacctt  19800
gcaatctcta caactatggt gctggtatta agttacctga tggcattatg tttaacgtag  19860
ttaaatacac acagctttgt caatatctca atagcaccac aatgtgtgta ccccatcaca  19920
tgcgtgtgct acatcttggt gctggctccg acaagggtgt tgcacctggc acggctgtct  19980
tacgacgttg gttgccactg gatgccatta tagttgacaa tgatagtgtg gattacgtta  20040
gcgatgctga ttatagtgtt acaggagatt gctctacctt atacctgtca gataagtttg  20100
atttagttat atctgatatg tatgatggta agattaaaag ttgtgatggg gagaacgtgt  20160
ctaaagaagg cttctttccc tatgttaatg gtgtcatcac cgaaaagttg gcacttggtg  20220
gtactgtagc tattaaggtg acggagttta gttggaataa gaagttgtat gaactcattc  20280
agaggtttga gtattggaca atgttctgta ccagtgttaa cacgtcatcg tcagaggcat  20340
tcttaattgg tgttcactat ttaggtgatt ttgcaagtgg cgctgtgatt gacggcaaca  20400
ctatgcatgc caattatatc ttctggcgta attccacaat tatgactatg tcttacaata  20460
gtgtacttga tttaagcaag ttcaattgta agcataaggc tacagttgtc attaatttaa  20520
aagattcatc cattagtgat gttgtgttag gtttgttgaa gaatggtaag ttgctagtgc  20580
gtaataatga cgccatttgt ggtttttcta atcatttggt caacgtaaac aaatgaagtc  20640
tttaacctac ttctggttgt tcttaccagt actttcaaca cttagcctac cacaagatgt  20700
caccaggtgc tcagctaaga ctaattttag gcggttcttt tcaaaattta atgttcaggc  20760
gcctgcagtt gttgtactgg gcggttatct acctattggt gaaaaccagg gtgtcaattc  20820
aacttggtac tgtgctggcc aacatccaac tgctagtggc gttcatggta tctttgttag  20880
ccatattaga ggtggtcatg gctttgagat tggcatttcg caagagcctt ttgaccctag  20940
tggttaccag ctttatttac ataaggctac taacggtaac actaatgcta ctgcgcgact  21000
gcgcatttgc cagtttccta gcattaaaac attgggcccc actgctaata atgatgttac  21060
aataggtcgt aattgcctat ttaacaaagc catcccagct catatgagtg aacatagtgt  21120
tgtcggcata acatgggata atgatcgtgt cactgtcttt tctgacaaga tctattattt  21180
ttattttaaa aatgattggt cccgtgttgc gacaaagtgt tacaacagtg gaggttgtgc  21240
```

```
tatgcaatat gtttacgaac ccacctatta catgcttaat gttactagtg ctggtgagga  21300
tggtatttct tatcaaccct gtacagctaa ttgcattggt tatgctgcca atgtatttgc  21360
tactgagccc aatggccaca taccagaagg ttttagtttt aataattggt ttcttttgtc  21420
caatgattcc actttggtgc atggtaaggt ggtttccaac caaccattgt tggtcaattg  21480
tcttttggcc attcctaaga tttatggact aggccaattt ttctccttta atcaaacgat  21540
cgatggtgtt tgtaatggag ctgctgtgca gcgtgcacca gaggctctga ggtttaatat  21600
taatgacacc tctgtcattc ttgctgaagg ctcaattgta cttcatactg ctttaggaac  21660
aaatttttct tttgtttgca gtaattcctc aaatcctcac ttagccacct tcgccatacc  21720
tttgggtgct acccaagtac cctattattg ttttttaaa gtggatactt acaactccac  21780
tgtttataaa ttcttggctg ttttacctcc aaccgtcagg gaaattgtca tcaccaagta  21840
tggtgatgtt tatgtcaatg ggtttggata cttgcatctc ggtttgttgg atgctgtcac  21900
aattaatttc actggtcatg gcactgacga tgatgtttct ggtttttgga ccatagcatc  21960
gactaatttt gttgatgcac tcatcgaagt tcaaggaacc gccattcagc gtattcttta  22020
ttgtgatgat cctgttagcc aactcaagtg ttctcaggtt gcttttgacc ttgacgatgg  22080
tttttaccct ttttcttcta gaaaccttct gagtcatgaa cagccaattt cttttgttac  22140
tctgccatca tttaatgctc attcttttgt taacattact gtatctgctt cctttggtgg  22200
tcatagtggt gccaacctta ttgcatctga cactactatc aatgggttta gttctttctg  22260
tgttgacact agacaattta ccatttcact gtcttataac gttacaaaca gttatggtta  22320
tgtgtctaac tcacaggaca gtaattgccc tttcaccttg caatctgtta atgattacct  22380
gtcttttagc aaattttgtg tttccaccag cctttttggct agtgcctgta ccatagatct  22440
ttttggttac cctgagtttg gtagtggtgt taagtttacg tccctttact ttcaattcac  22500
aaagggtgag ttgattactg gcacgcctaa accacttgaa ggtgtcacgg acgtttcttt  22560
tatgactctg gatgtgtgta ccaagtatac tatctatggc tttaaaggtg agggtatcat  22620
tacccttaca aattctagct tttggcagg tgtttattac acatctgatt ctggacagtt  22680
gttagccttt aagaatgtca ctagtggtgc tgtttattct gttacgccat gttcttttc  22740
agagcaggct gcatatgttg atgatgatat agtgggtgtt atttctagtt tgtctagctc  22800
cacttttaac agtactaggg agttgcctgg tttcttctac cattctaatg atggctctaa  22860
ttgtacagag cctgtgttgg tgtatagtaa cataggtgtt tgtaaatctg gcagtattgg  22920
ctacgtccca tctcagtctg gccaagtcaa gattgcaccc acggttactg ggaatattag  22980
tattcccacc aactttagta tgagtattag gacagaatat ttacagcttt acaacacgcc  23040
tgttagtgtt gattgtgcca catatgtttg taatggtaac tctcgttgta aacaattact  23100
cacccagtac actgcagcat gtaagaccat agagtcagca ttacaactca gcgctaggct  23160
tgagtctgtt gaagttaact ctatgcttac tatttctgaa gaggctctac agttagctac  23220
cattagttcg tttaatggtg atggatataa ttttactaat gtgctgggtg tttctgtgta  23280
tgatcctgca cgtggcaggg tggtacaaaa aaggtctttt attgaagacc tgctttttaa  23340
taaagtggtt actaatggcc ttggtactgt tgatgaagac tataagcgct gttctaatgg  23400
tcgctctgtg gcagatctag tctgtgcaca gtattactct ggtgtcatgg tactacctgg  23460
tgttgttgac gctgagaagc ttcacatgta tagtgcgtct ctcatcggtg gtatggtgct  23520
aggaggtttt actgctgcag cggcattgcc ttttagctat gctgttcaag ctagactcaa  23580
ttatcttgct ctacagacgg atgttctaca gcggaaccag caattgcttg ctgagtcttt  23640
```

```
taactctgct attggtaata taacttcagc ctttgagagt gttaaagagg ctagtagtca  23700
aacttccagg ggtttgaaca ctgtggctca tgcgcttact aaggttcaag aggttgttaa  23760
ctcgcagggt gcagctttga ctcaacttac cgtacagctg caacacaact tccaagccat  23820
ttctagttct attgatgaca tttactctcg actggacatt ctttcagccg atgttcaggt  23880
tgaccgtctc atcaccggca gattatcagc acttaatgct tttgttgctc aaaccctcac  23940
taagtatact gaggttcagg ctagcaggaa gttagcacag caaaaggtta atgagtgcgt  24000
taaatcgcaa tctcagcgtt atggtttttg tggtggtgat ggcgagcaca ttttctctct  24060
ggtacaggca gcacctcagg gcctgctgtt tttacataca gtacttgtac cgagtgattt  24120
tgtagatgtt attgccatcg ctggcttatg cgttaacgat gaaattgcct tgactctacg  24180
tgagcctggc ttagtcttgt ttacgcatga acttcaaaat catactgcga cggaatattt  24240
tgtttcatcg cgacgtatgt ttgaacctag aaaacctacc gttagtgatt ttgttcaaat  24300
tgagagttgt gtggtcacct atgtcaattt gactagagac caactaccag atgtaatccc  24360
agattacatc gatgttaaca aaacacgtga tgagatttta gcttctctgc ccaatagaac  24420
tggtccaagt cttcctttag atgtttttaa tgccacttat cttaatctca ctggtgaaat  24480
tgcagattta gagcagcgtt cagagtctct ccgtaatact acagaggagc tccaaagtct  24540
tatatataat atcaacaaca cactagttga ccttgagtgg ctcaaccgag ttgagacata  24600
tatcaagtgg ccgtggtggg tttggttgat tattttcatt gttctcatct ttgttgtgtc  24660
attactagtg ttctgctgca tttccacggg tttttgtgga tgcttcggct gctgctgtgc  24720
ttgtttctca ggttgttgta ggggtcctag acttcaacct tacgaagttt ttgaaaaggt  24780
ccacgtgcag tgatgtttct tggacttttt caatacacga ttgacacagt tgtcaaagat  24840
gtctcaaagt ctgctaactt gtctttggat gctgtccaag agttggagct caatgtagtt  24900
ccaattagac aagcttcaaa tgtgacgggt tttcttttca ccagtgtttt tatctacttc  24960
tttgcactgt ttaaagcgtc ttctttgagg cgcaattatg ttatgttggc agcgcgtttt  25020
gctgtcattg ttctttattg cccacttta tattattgtg gtgcattttt agatgcaact  25080
gttatttgtt gcacacttat tggcaggctt tgtttagtct gcttttactc ctggcgctat  25140
aaaaatgcgc tctttattat ttttaatact acgacacttt ctttcctcaa tggtaaagca  25200
gcttattatg acggcaaatc cattgtgatt ttagaaggtg gtgaccatta catcactttt  25260
ggcaactctt ttgttgcttt tgttagtagc atcgacttgc atctagctat acgtgggcgg  25320
caagaagctg acctacagct gttgcgaact gttgagcttc ttgatggcaa gaagctttat  25380
gtcttttcgc aacatcaaat tgttggcatt actaatgctg catttgactc aattcaacta  25440
gacgagtatg ctacaattag tgaatgataa tggtctagta gttaatgtta tactttggct  25500
tttcgtactc tgttttctgc ttattataag cattactttc gtccaattgg ttaatctgtg  25560
cttcacttgt caccggttgt gtaatagcgc agtttacaca cctatagggc gtttgtatag  25620
agtttataag ttttacatgc aaatagaccc cctccctagt actgttattg acgtataaac  25680
gaaatatgtc taacggttct attcccgttg atgaggtggt tcaacacctt agaaactgga  25740
atttcacatg gaatatcata ctgacgatac tacttgtagt gcttcagtat ggccattaca  25800
agtactctgc gttcttgtat ggtgtcaaga tggctattct atggatactt tggcctcttg  25860
tgttagcact gtcacttttt gatgcatggg ctagctttca ggtcaattgg gtcttttttg  25920
ctttcagcat ccttatggct tgcatcactc ttatgctgtg gataatgtac tttgtcaata  25980
```

-continued

```
gcattcggtt gtggcgcagg acacattctt ggtggtcttt caatcctgaa acagacgcgc  26040
ttctcactac ttctgtgatg ggccgacagg tctgcattcc agtgcttgga gcaccaactg  26100
gtgtaacgct aacactcctt agtggtacat tgcttgtaga gggctataag gttgctactg  26160
gcgtacaggt aagtcaatta cctaatttcg tcacagtcgc caaggccact acaacaattg  26220
tctacggacg tgttggtcgt tcagtcaacg cttcatctgg cactggttgg gctttctatg  26280
tccgatccaa acacggcgac tactcagctg tgagtaatcc gagttcggtt ctcacagata  26340
gtgagaaagt gcttcattta gtctaaacag aaactttatg gcttctgtca gttttcagga  26400
tcgtggccgc aaacgggtgc cattatccct ctatgcccct cttagggtta ctaatgacaa  26460
accccttct aaggtacttg caaataatgc tgtacccact aataaaggaa ataaggacca  26520
gcaaattgga tactggaatg agcaaattcg ctggcgcatg cgccgtggtg agcgaattga  26580
acaaccttcc aattggcatt tctactacct cggaacagga cctcacgccg acctccgcta  26640
taggactcgt actgagggtg ttttctgggt tgctaaagaa ggcgcaaaga ctgaacccac  26700
taacctgggt gtcagaaagg cgtctgaaaa gccaattatt ccaaatttct ctcaacagct  26760
tcccagcgta gttgagattg ttgaacctaa cacacctcct acttcacgtg caaattcacg  26820
tagcaggagt cgtggtaatg gcaacaacag gtccagatct ccaagtaaca acagaggcaa  26880
taaccagtcc cgcggtaatt cacagaatcg tggaaataac cagggtcgtg gagcttctca  26940
gaacagagga ggcaataata ataacaataa caagtctcgt aaccagtcca agaacagaaa  27000
ccagtcaaat gaccgtggtg gtgtaacatc acgcgatgat ctggtggctg ctgtcaagga  27060
tgcccttaaa tctttgggta ttggcgaaaa ccctgacaag cttaagcaac agcagaagcc  27120
caaacaggaa aggtctgaca gcagcggcaa aaatacacct aagaagaaca aatccagagc  27180
cacttcgaaa gaacgtgacc tcaaagacat cccagagtgg aggagaattc ccaagggcga  27240
aaatagcgta gcagcttgct tcggacccag gggaggcttc aaaaatttttg gagatgcgga  27300
atttgtcgaa aaaggtgttg atgcctcagg ctatgctcag atcgccagtt tagcaccaaa  27360
tgttgcagca ttgctctttg gtggtaatgt ggctgttcgt gagctagcgg actcttacga  27420
gattacatat aattataaaa tgactgtgcc aaagtctgat ccaaatgtag agcttcttgt  27480
ttcacaggtg gatgcattta aaactgggaa tgcaaaaccc cagagaaaga aggaaaagaa  27540
gaacaagcgt gaaaccacgc agcagctgaa tgaagaggcc atctacgatg atgtgggtgt  27600
gccatctgat gtgactcatg ccaatttgga atgggacaca gctgttgatg gtggtgacac  27660
ggccgttgaa attatcaacg agatcttcga cacaggaaat taaacaatgt ttgactggct  27720
tatcctggct atgtcccagg gtagtgccat tacactgtta ttactgagtg tttttctagc  27780
gacttggctg ctgggctatg gctttgccct ctaactagcg gtcttggtct tgcacacaac  27840
ggtaagccag tggtaatgtc agtgcaagaa ggatattacc atagcactgt catgagggga  27900
acgcagtacc ttttcatcta aacctttgca cgagtaatca aagatccgct tgacgagcct  27960
atatggaaga gcgtgccagg tatttgaccc aaggactgtt agtaactgaa gacctgacgg  28020
tgttgatatg gatacgcaaa aaaaaaaaaa aaaaaaaaaa aaa                    28063
```

VACCINE COMPOSITION AND METHOD OF PREVENTING PORCINE EPIDEMIC DIARRHEA VIRUS INFECTION IN SWINE

CROSS-REFERENCE TO RELATED APPLICATION

This application claims the priority benefit of U.S. provisional application Ser. No. 62/894,867, filed on Sep. 2, 2019. The entirety of the above-mentioned patent application is hereby incorporated by reference herein and made a part of this specification.

BACKGROUND

Technical Field

The present invention generally relates to a vaccine composition, in particular, relates to a method of preventing porcine epidemic diarrhea virus (PEDV) infection in swine by using the vaccine composition.

Description of Related Art

Porcine epidemic diarrhea virus (PEDV) is an alphacoronavirus that infects the lining of the swine's small intestine cells, which causes porcine epidemic diarrhea. Swine infected with PEDV usually have symptoms such as vomiting, anorexia, dehydration, watery diarrhea, and weight loss. Newborn piglets infected with PEDV have a high mortality rate, and usually die within five days of contracting the virus, whereas piglets older than 10 days have a lowered mortality rate, and mostly get sick and lose weight after being infected. PEDV presents a significant economic burden with its high morbidity and mortality rate in piglets, thus a vaccine that provides protection against PEDV is urgently required.

Currently, the available PEDV vaccine has encountered many problems. For example, the conventional vaccine was found to be ineffective in inducing Immunoglobulin A (IgA), hence, the immune protection was thought to be insufficient and limited. Further studies are still required for providing a vaccine with sufficient protection against PEDV.

SUMMARY

Accordingly, the present disclosure is directed to a vaccine composition that may be used for preventing porcine epidemic diarrhea virus (PEDV) infection in swine, and may provide sufficient immune protection.

In accordance with some embodiments of the present disclosure, a vaccine composition is provided. The vaccine composition includes a porcine epidemic diarrhea virus (PEDV) S1 spike protein having an amino acid sequence of SEQ ID NO: 1, and an inactivated porcine epidemic diarrhea virus (PEDV).

In the above embodiment, a concentration of the PEDV S1 spike protein is in a range of about 15 μg/dose to about 75 μg/dose.

In the above embodiment, the concentration of the PEDV S1 spike protein is in a range of about 20 μg/dose to about 40 μg/dose.

In the above embodiment, the concentration of the PEDV S1 spike protein is about 30 μg/dose.

In the above embodiment, a concentration of the inactivated PEDV is in a range of about $1*10^6$ of 50% Tissue culture Infective Dose ($TCID_{50}$)/dose to about $1*10^9$ $TCID_{50}$/dose.

In the above embodiment, a concentration of the inactivated PEDV is in a range of about $1*10^6$ of 50% Tissue culture Infective Dose ($TCID_{50}$)/dose to about $1*10^7$ $TCID_{50}$/dose.

In the above embodiment, the PEDV S1 spike protein has a nucleotide sequence of SEQ ID NO: 2.

In the above embodiment, the PEDV S1 spike protein is further modified with a signal peptide to obtain a nucleotide sequence of SEQ ID NO: 3.

In the above embodiment, the vaccine composition further includes adjuvants, wherein a concentration of the adjuvants is in a range of 55% by weight to 65% by weight based on a total weight of the vaccine composition.

In the above embodiment, the inactivated PEDV has a nucleotide sequence of SEQ ID NO: 4.

In accordance with another embodiment of the present disclosure, a method of preventing porcine epidemic diarrhea virus (PEDV) infection in swine is described. The method includes vaccinating a pregnant sow with the vaccine composition described above at least three weeks prior to farrowing to confer immunity to the neonatal piglets.

In the above embodiment, the pregnant sow is vaccinated by administering a first dose of the vaccine composition eight weeks prior to farrowing, and administering a second dose of the vaccine composition five weeks prior to farrowing.

In yet another embodiment of the present disclosure, a vaccine composition is provided. The vaccine composition includes a modified porcine epidemic diarrhea virus (PEDV) S1 spike protein having a nucleotide sequence of SEQ ID NO: 3, an inactivated porcine epidemic diarrhea virus (PEDV), and mineral oil-based adjuvants.

In the above embodiment, a concentration of the mineral oil-based adjuvants is in a range of 55% by weight to 65% by weight based on a total weight of the vaccine composition.

In the above embodiment, the inactivated PEDV has a nucleotide sequence of SEQ ID NO: 4.

By using the vaccine composition of the present disclosure for vaccination, systemic Immunoglobulin G (IgG), Immunoglobulin A (IgA) and neutralizing antibody against PEDV may be successfully induced, hence providing sufficient immune protection against PEDV.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

FIG. 2C illustrates the results of detecting the presence of neutralizing antibody in mice for different test groups from Example 2.

DESCRIPTION OF THE EMBODIMENTS

Figure 1A:
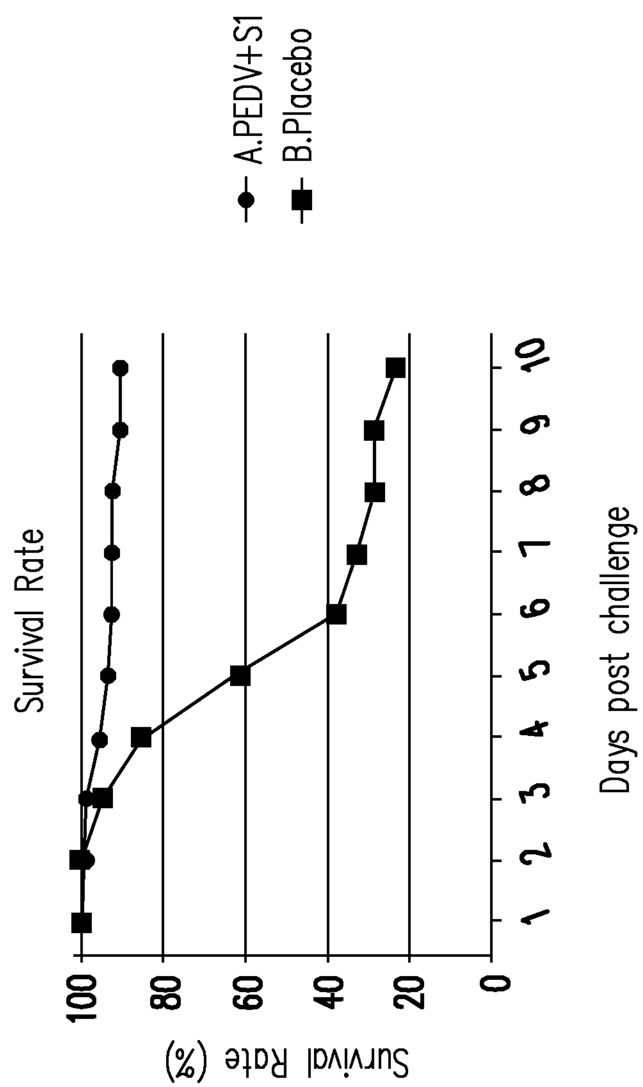
FIG. 1A is a graph illustrating the survival rate of the neonatal piglets challenged with the porcine epidemic diarrhea virus for different test groups from Example 1.

The present disclosure is directed to a vaccine composition for preventing porcine epidemic diarrhea virus (PEDV) infection in sows and piglets. In some exemplary embodiments, the vaccine composition may at least include a porcine epidemic diarrhea virus (PEDV) S1 spike protein having an amino acid sequence of SEQ ID NO: 1, and an inactivated porcine epidemic diarrhea virus (PEDV). The PEDV spike protein is a type I glycoprotein that can be divided into a S1 domain (amino acid 1-789) and a S2 domain (amino acid 790-1383). For example, the PEDV spike protein of the S1 domain is used as part of the vaccine composition, whereas the spike protein of the S2 domain is excluded from the vaccine composition.

In some embodiments, the PEDV S1 spike protein has an amino acid sequence of SEQ ID NO: 1, while having a nucleotide sequence of SEQ ID NO: 2. However, the disclosure is not limited thereto. In certain embodiments, the PEDV S1 spike protein may have a modified nucleotide sequence as long as it encodes the same amino acid sequence of SEQ ID NO: 1 or shares 95% sequence similarity to SEQ ID NO: 1. In some embodiments, the nucleotide sequence of SEQ ID NO: 2 may further include a signal peptide suitable for insect cell line expression. For example, the PEDV S1 spike protein may include a signal peptide and have a nucleotide sequence of SEQ ID NO: 3. Other types of signal peptide may be selected and used based on actual requirement.

In one exemplary embodiment, a concentration of the PEDV S1 spike protein is in a range of 15 μg/dose to 75 μg/dose of the vaccine. In some embodiments, the concentration of the PEDV S1 spike protein is in a range of 20 μg/dose to 40 μg/dose of the vaccine. In certain embodiments, the concentration of the PEDV S1 spike protein is 30 μg/dose of the vaccine. By adjusting the concentration of the PEDV S1 spike protein in such a range, sufficient immune protection against PEDV may be ensured.

Furthermore, in the vaccine composition, the inactivated porcine epidemic diarrhea virus (PEDV) may be any type or strain of porcine epidemic diarrhea virus that is inactivated. In other words, a killed PEDV vaccine is used. In one exemplary embodiment, the inactivated PEDV has a nucleotide sequence of SEQ ID NO: 4. However, the disclosure is not limited thereto. For example, other strains of inactivated PEDV having a modified nucleotide sequence may be used.

In one exemplary embodiment, a concentration of the inactivated PEDV is in a range of $1*10^6$ of 50% tissue culture infective dose ($TCID_{50}$)/dose to $1*10^9$ $TCID_{50}$/dose. In some embodiments, a concentration of the inactivated PEDV is in a range of $1*10^6$ of $TCID_{50}$/dose to $1*10^7$ $TCID_{50}$/dose. By adjusting the concentration of the inactivated PEDV in such a concentration range, sufficient immune protection against PEDV may be ensured.

In some embodiments, adjuvants may be further added into the vaccine composition in combination with the PEDV S1 spike protein and the inactivated PEDV. The adjuvants may be any type of adjuvants commonly used in the art, and the disclosure is not limited thereto. In one exemplary embodiment, the adjuvant used is a mineral oil-based adjuvant. For example, MONTANIDE™ ISA 61 VG obtained from SEPPIC Inc. may be used as the mineral oil-based adjuvant. In some embodiments, a concentration of the adjuvants is in a range of 55% by weight to 65% by weight based on a total weight of the vaccine composition. In one exemplary embodiment, the concentration of the adjuvants is 60% by weight based on a total weight of the vaccine composition.

By designing the vaccine composition to include at least a PEDV S1 spike protein having an amino acid sequence of SEQ ID NO: 1, and an inactivated porcine epidemic diarrhea virus (PEDV), systemic Immunoglobulin G (IgG), Immunoglobulin A (IgA) and neutralizing antibody against PEDV may be successfully induced, hence providing sufficient immune protection.

A method of preventing porcine epidemic diarrhea virus (PEDV) infection in swine can be achieved by using the vaccine composition described above. For example, in some embodiments, a pregnant sow is vaccinated with the vaccine composition at least three weeks prior to farrowing to confer immunity to its neonatal piglets. In one exemplary embodiment, the pregnant sow is vaccinated by administering a first dose of the vaccine composition eight weeks prior to farrowing, and administering a second dose of the vaccine composition five weeks prior to farrowing. The pregnant sow may be further vaccinated by administering a third dose of the vaccine composition three weeks prior to farrowing. However, the disclosure is not limited thereto. In some other embodiments, the pregnant sow is vaccinated by administering a first dose of the vaccine composition five weeks prior to farrowing, and administering a second dose of the vaccine composition three weeks prior to farrowing. Alternatively, the pregnant sow only needs to be vaccinated with one dose of the vaccine composition at least three weeks prior to farrowing to confer immunity to its neonatal piglets.

By using the method of preventing porcine epidemic diarrhea virus (PEDV) infection in swine described above, sufficient immune protection against PEDV may be ensured.

EXAMPLES

The following experimental examples are performed to prove that the vaccine composition of the present disclosure can successfully induce Immunoglobulin G (IgG), Immunoglobulin A (IgA) and neutralizing antibody, so that sufficient immune protection against PEDV can be conferred.

Example 1

In this example, 10 pregnant sows were randomly selected and divided into two groups (Group A and Group B) for evaluation. In Group A (PEDV+S1), 8 pregnant sows were vaccinated with a vaccine composition including the following components: (a) inactivated PEDV having a nucleotide sequence of SEQ ID NO: 4 (PEDVPT) with a concentration of $1*10^7$ $TCID_{50}$/dose; (b) PEDV S1 spike protein having a nucleotide sequence of SEQ ID NO: 3 with a concentration of 30 μg/dose; and (c) MONTANIDE™ ISA 61 VG obtained from SEPPIC Inc. as the adjuvant with a concentration of 60% by weight based on a total weight of the vaccine composition. In Group B (Placebo/Control), 2 pregnant sows were administered with a composition containing only MONTANIDE™ ISA 61 VG obtained from SEPPIC Inc. as the adjuvant.

The pregnant sows were respectively injected or vaccinated with the compositions described in Group A and Group B by administering a first dose of the composition eight weeks prior to farrowing, administering a second dose of the composition five weeks prior to farrowing, and administering a third dose of the composition three weeks prior to farrowing, wherein 2 mL of the composition were administered for each dose. After farrowing, the neonatal piglets from Group A and Group B were challenged with the porcine epidemic diarrhea virus so as to evaluate the effect of preventing PEDV infection. The evaluation results are presented in FIG. 1A.

FIG. 1A is a graph illustrating the survival rate of the neonatal piglets challenged with the porcine epidemic diarrhea virus for different test groups from Example 1. As illustrated in FIG. 1A, the survival rate of the neonatal piglets in Group A (vaccinated) was 89.6% (52/58 neonatal piglets survived), whereas the survival rate of the neonatal piglets in Group B (Placebo) was 24% (5/21 neonatal piglets survived) after 10 days of challenging the neonatal piglets with PEDV. The results suggest that the vaccine composition of the present disclosure is successful in improving the survival rate of neonatal piglets challenged with PEDV. In other words, sufficient immune protection was conferred.

In order to evaluate the ability of the vaccine composition to induce Immunoglobulin G (IgG), Immunoglobulin A (IgA) and neutralizing antibody in pregnant sows, serum and oral swab from the pregnant sows from Group A and Group B were collected and evaluated. The serum and oral swabs were collected after each vaccination (three vaccinations in total) and after farrowing.

A S-protein based indirect enzyme-linked immunosorbent assay (ELISA) was performed to quantitate the presence of IgG in the serum by the following steps. In an ELISA microplate, RECOMBINANT PEDV S1 protein was added at a concentration of 200 ng/well using coating buffer A for coating. The microplate was incubated at 4° C. overnight, and then washed with 1× PBST (phosphate buffered saline with Tween 20) for four times. Subsequently, 250 μL of blocker (5% skim milk) (blocking buffer) was added to each of the wells and kept at room temperature for 1 hour. The microplate was then washed with 1× PBST for four times. The collected serum samples (100 μL; diluted 40 times) were then added to each of the wells and kept at 37° C. for 1 hour. Subsequently, 100 μL of secondary antibody (horseradish peroxidase conjugated anti-swine IgG (Swine-IgG-HRPO)) was added to each of the wells and kept at 37° C. for 1 hour. The microplate was then washed with 1× PBST for four times, and 100 μL of 3,3',5,5'-Tetramethylbenzidine (TMB) was added to each of the wells to allow color development for 10 minutes at room temperature. Thereafter, the reaction was terminated by adding 100 μL of stop solution to each of the wells, and the amount of IgG in the serum was quantitated using an ELISA reader at 450 nm. The evaluation results are presented in FIG. 1B.

Figure 1B:
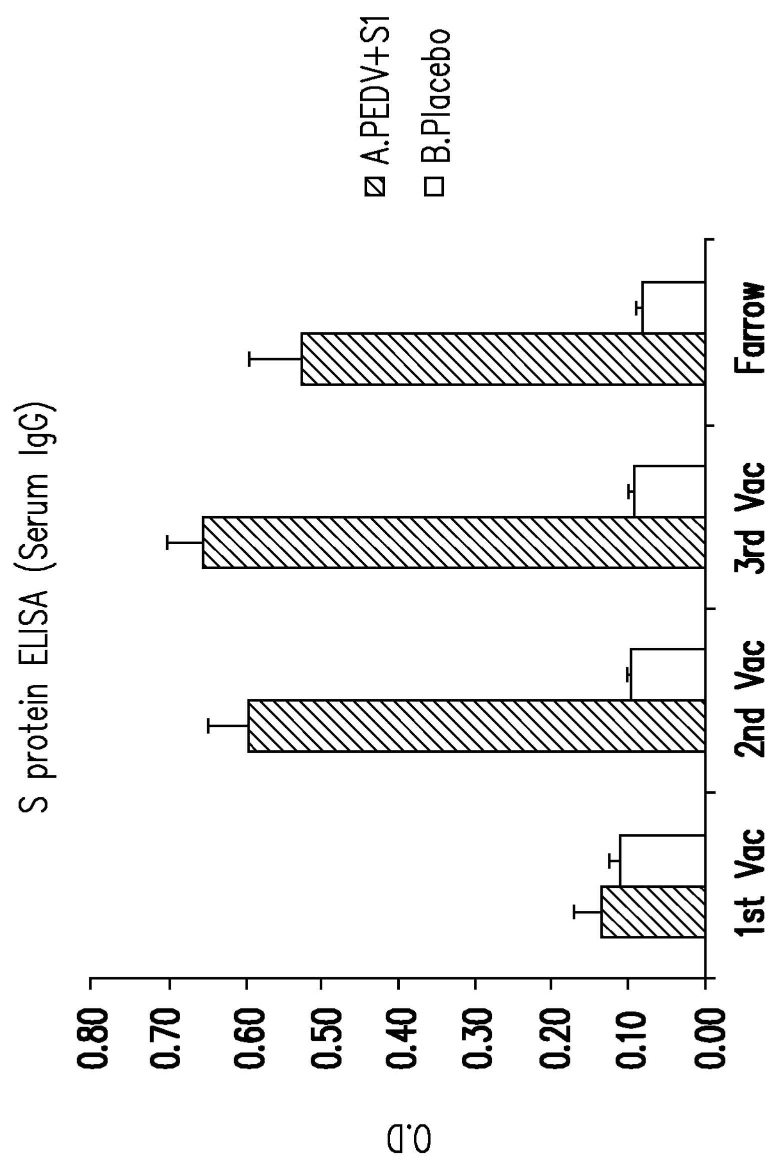
FIG. 1B illustrates the results from ELISA for detecting the presence of IgG for different test groups from Example 1.

FIG. 1B illustrates the results from ELISA for detecting the presence of IgG for different test groups from Example 1. As illustrated in FIG. 1B, the concentration of IgG detected in Group A (PEDV+S1) was slightly higher than the concentration of IgG detected in Group B (Placebo) after the first vaccination (administering the first dose). Furthermore, the concentration of IgG in Group A (PEDV+S1) significantly increased after the second vaccination (administering the second dose), whereas the concentration of IgG detected in Group B (Placebo) was found to be substantially constant. The difference in the IgG levels in Group A and Group B was also observed in the third vaccination and after farrowing. These results suggest that the vaccine composition of the present disclosure is successful in inducing IgG to provide sufficient immune protection.

In a similar way, a S-protein based indirect enzyme-linked immunosorbent assay (ELISA) was performed to quantitate the presence of IgA in the oral swab by the following steps. First of all, the collected oral swab was weighted and immersed in 1 mL of 1× PBS (phosphate buffered saline) and placed at 4° C. for 10 minutes. The saliva was then centrifuged at 3,500×g for 10 minutes at 4° C., and the supernatant was collected. The supernatant was then stored at −80° C. until use. For ELISA, RECOMBINANT PEDV S1 protein was added at a concentration of 200 ng/well using coating buffer A for coating onto an ELISA microplate. The microplate was kept at 4° C. overnight, and then washed with 1× PBST (phosphate buffered saline with Tween 20) for four times. Subsequently, 250 μL of blocker (5% skim milk) (blocking buffer) was added to each of the wells and kept at room temperature for 1 hour. The microplate was then washed with 1× PBST for four times. Dispense 100 μL of collected supernatant samples into the appropriate wells. Tap the holder to remove air bubbles from the liquid and mix well. Incubate for 2 hours at 37° C. The microplate was then washed with 1× PBST for four times. Subsequently, 100 μL of secondary antibody (horseradish peroxidase conjugated goat anti-swine IgA (Swine-IgA-HRPO)) was added to each of the wells and kept at 37° C. for 1 hour. The microplate was then washed with 1× PBST for four times, and 100 μL of 3,3',5,5'-Tetramethylbenzidine (TMB) was added to each of the wells to allow color development for 10 minutes at room temperature. Thereafter, the reaction was terminated by adding 100 μL of stop solution to each of the wells, and the amount of IgA in the supernatant samples was quantitated using an ELISA reader at 450 nm. The evaluation results are presented in FIG. 1C.

Figure 1C:
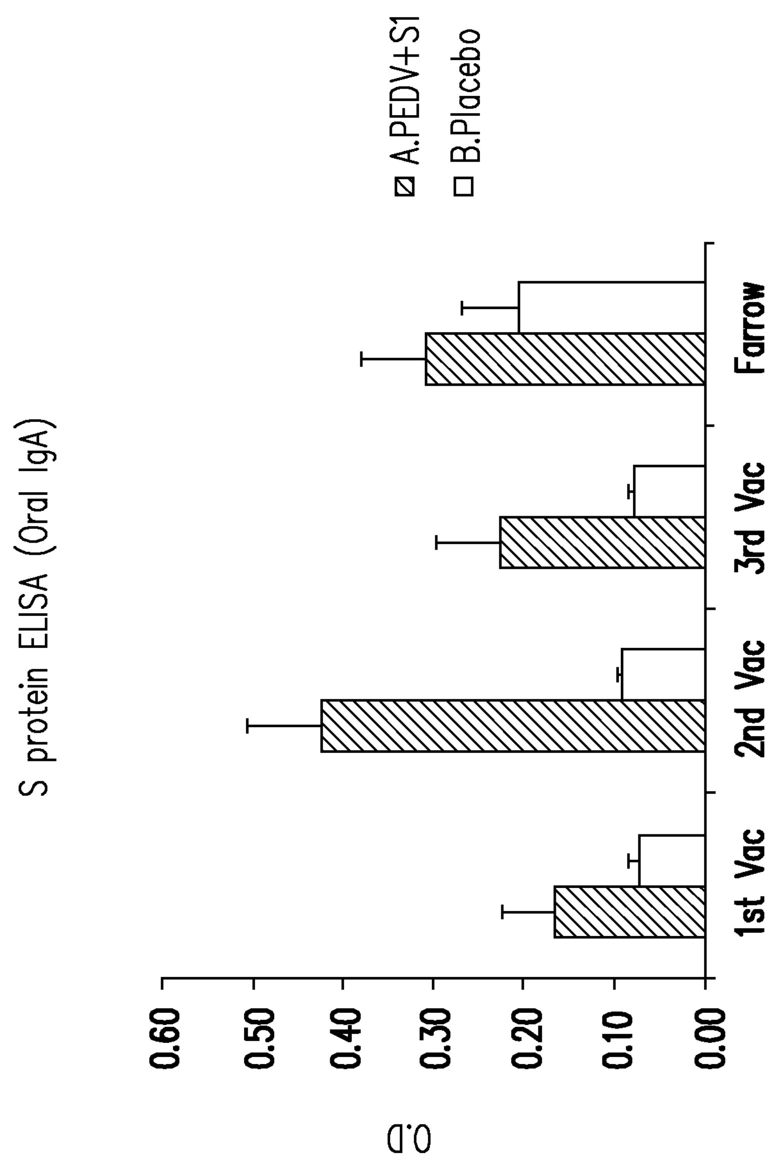
FIG. 1C illustrates the results from ELISA for detecting the presence of IgA for different test groups from Example 1.

FIG. 1C illustrates the results from ELISA for detecting the presence of IgA for different test groups from Example 1. As illustrated in FIG. 1C, the concentration of IgA detected in Group A (PEDV+S1) was slightly higher than the concentration of IgA detected in Group B (Placebo) after the first vaccination. Furthermore, the concentration of IgA in Group A (PEDV+S1) significantly increased after the second vaccination, whereas the concentration of IgA detected in Group B (Placebo) was found to be substantially constant. The difference in the IgA levels in Group A and Group B was still observed in the third vaccination and after farrowing. However, it is noted that the IgA levels of Group B also slightly increased after farrowing. These results suggest that the vaccine composition of the present disclosure is successful in inducing IgA to provide sufficient immune protection.

The neutralizing antibody titers in the serum of the sows from Group A (PEDV+S1) and Group B (Placebo) was also evaluated and the results are presented in Table 1 shown below.

TABLE 1

| Groups | Number of Piglets Born | Number of Piglets Tested | Number of Piglets survived | Survival Rate (%) | Neutralizing Antibody (NA) titer |
|---|---|---|---|---|---|
| Group A | 4 | 4 | 4 | 100.00 | 640 |
| (PEDV + | 4 | 4 | 4 | 100.00 | 80 |
| S1) | 10 | 8 | 6 | 75.00 | 320 |
| | 10 | 10 | 10 | 100.00 | 160 |
| | 5 | 5 | 5 | 100.00 | 160 |
| | 6 | 6 | 6 | 100.00 | 80 |
| | 9 | 9 | 7 | 77.78 | 160 |
| | 12 | 12 | 10 | 83.33 | 160 |

TABLE 1-continued

| Groups | Number of Piglets Born | Number of Piglets Tested | Number of Piglets survived | Survival Rate (%) | Neutralizing Antibody (NA) titer |
|---|---|---|---|---|---|
| Group B | 13 | 13 | 1 | 7.69 | 20 |
| (Placebo) | 8 | 8 | 4 | 50.00 | 20 |

As shown in Table 1, the neonatal piglets in Group A (vaccinated) had an overall higher survival rate. In comparison, the neonatal piglets in Group B (Placebo) had a lower survival rate. Sows in Group A had higher neutralizing antibody titers while sows in Group B had lower neutralizing antibody titers. These results suggest that the vaccine composition of the present disclosure is successful in inducing neutralizing antibody to provide sufficient immune protection.

Example 2

In Example 1, the vaccine composition of the present disclosure was found to be successful in inducing Immunoglobulin G (IgG), Immunoglobulin A (IgA) and neutralizing antibody, so that sufficient immune protection against PEDV can be conferred. However, the roles of each of the inactivated PEDV and the PEDV S1 spike protein components of the vaccine composition in inducing the observed immunogenic effects is unclear. In the current example, three weeks old BALB/c mice were tested in groups of five for immunological evaluation. The samples for immunological evaluation were prepared according to the groups shown in Table 2.

TABLE 2

| Vaccine Groups | Weight per dose | Oil Phase | Water Phase | |
|---|---|---|---|---|
| Group A (Placebo) | 7.5 g | 4.5 g ISA61 | Inactivated PEDV | — |
| | | | S1 spike protein | — |
| | | | PBS | 3.0 mL |
| Group B (PEDV) | 7.5 g | 4.5 g ISA61 | Inactivated PEDV | 0.71 mL |
| | | | S1 spike protein | — |
| | | | PBS | 2.29 mL |
| Group C (S1) | 7.5 g | 4.5 g ISA61 | Inactivated PEDV | — |
| | | | S1 spike protein | 1.5 mL |
| | | | PBS | 1.5 mL |
| Group D (PEDV + S1) | 7.5 g | 4.5 g ISA61 | Inactivated PEDV | 0.71 mL |
| | | | S1 spike protein | 1.50 mL |
| | | | PBS | 0.79 mL |

Referring to Table 2, in Group A (Placebo), mice in groups of five were administered with a composition containing only MONTANIDE™ ISA 61 VG obtained from SEPPIC Inc. as the adjuvant. In Group B (PEDV), mice in groups of five were administered with a composition containing: (a) inactivated PEDV having a nucleotide sequence of SEQ ID NO: 4 (PEDVPT) with a concentration of $1*10^6$ $TCID_{50}$/dose; and (b) MONTANIDE™ ISA 61 VG obtained from SEPPIC Inc. as the adjuvant with a concentration of 60% by weight based on a total weight of the vaccine composition. In Group C (S1), mice in groups of five were administered with a composition containing: (a) PEDV S1 spike protein having a nucleotide sequence of SEQ ID NO: 3 with a concentration of 3 μg/dose; and (b) MONTANIDE™ ISA 61 VG obtained from SEPPIC Inc. as the adjuvant with a concentration of 60% by weight based on a total weight of the vaccine composition. In Group D (PEDV+S1), mice in groups of five were administered with a composition containing: (a) inactivated PEDV having a nucleotide sequence of SEQ ID NO: 4 (PEDVPT) with a concentration of $1*10^6$ $TCID_{50}$/dose; (b) PEDV S1 spike protein having a nucleotide sequence of SEQ ID NO: 3 with a concentration of 3 μg/dose; and (c) MONTANIDE™ ISA 61 VG obtained from SEPPIC Inc. as the adjuvant with a concentration of 60% by weight based on a total weight of the vaccine composition.

Furthermore, referring to Table 2, the vaccine compositions were prepared by adding the water phase to the oil phase by mixing at 8,000 rpm for 30 seconds, and then mixing at 16,000 rpm for three minutes to obtain an emulsion. The emulsion was stored at 4° C. until use. The mice were injected or vaccinated with the compositions described in Groups A to D of Table 2 by administering a first dose of the composition at the first day (week 0; W0), then administering a second dose of the composition at the third week (week 3; (W3), wherein 100 μL of the composition were administered for each dose. Serum and stool of the mice from Groups A to D were then collected every week. The mice were then sacrificed after 6 weeks, and the intestine was also collected. A S-protein based indirect enzyme-linked immunosorbent assay (ELISA) was then performed to quantitate the presence of IgG/IgA in the serum, stool and intestines. Serum IgG was measured in serum samples that were collected weekly after $1^{st}$ vaccination (W0~W6). The concentration of IgA was measured by ELISA with stool samples collected at 0~5 weeks after $1^{st}$ vaccination (W0~W5) and with intestine samples collected at W6.

In brief, to quantitate IgG in serum, RECOMBINANT PEDV S1 protein was added at a concentration of 200 ng/well using coating buffer A for coating onto an ELISA microplate. The microplate was incubated at 4° C. overnight, and then washed with 1× PBST for four times. Subsequently, 250 μL of blocker (5% skim milk) was added to each of the wells and kept at room temperature for 1 hour. The microplate was then washed with 1× PBST for four times. The collected serum samples (100 μL; diluted 40 times) were then added to each of the wells and kept at 37° C. for 1 hour. Subsequently, 100 μL of secondary antibody (Mouse-IgG-HRPO, diluted 10,000 times) was added to each of the wells and kept at 37° C. for 1 hour. The microplate was then washed with 1× PBST for four times, and 100 μL of 3,3',5,5'-Tetramethylbenzidine (TMB) was added to each of the wells to allow color development for 10 minutes at room temperature. Thereafter, the reaction was terminated by adding 100 μL of stop solution to each of the wells, and the amount of IgG in the serum was quantitated using an ELISA reader at 450 nm. The evaluation results are presented in FIG. 2A.

Figure 2A:
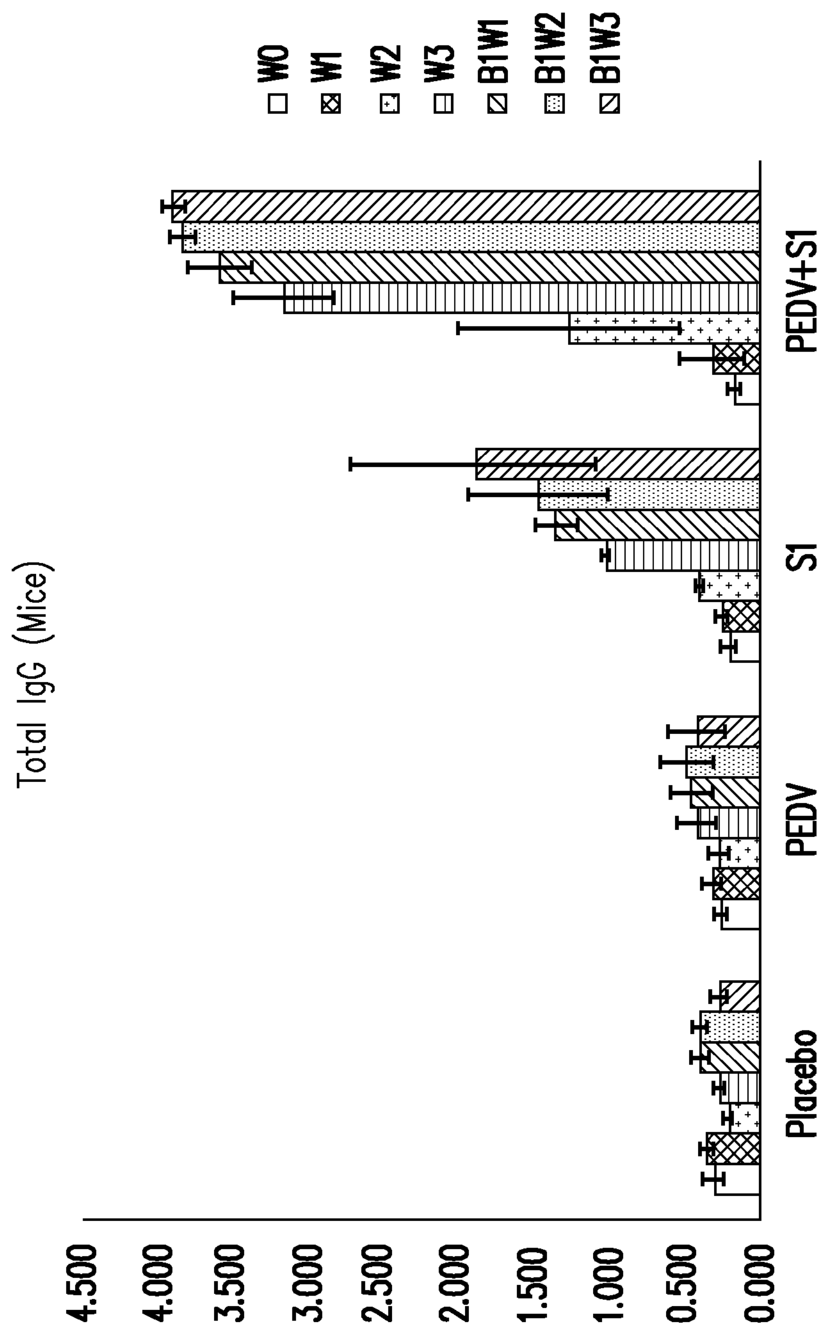
FIG. 2A illustrates the results from ELISA for detecting the presence of IgG in mice for different test groups from Example 2.

FIG. 2A illustrates the results from ELISA for detecting the presence of IgG in mice for different test groups from Example 2. As illustrated in FIG. 2A, the increase of the detected IgG levels was most apparent in Group C (S1) and Group D (PEDV+S1) after the first vaccination and the second vaccination. However, it is clear that the mice administered with the composition of Group D showed the most significant increase in the IgG levels. These results indicate that the combination of inactivated PEDV and PEDV S1 spike protein in the vaccine composition is important in inducing high levels of IgG. In comparison, inactivated PEDV with adjuvants alone (Group B) were unsuccessful in inducing IgG, and showed IgG levels that are similar to the control (Group A). Furthermore, although PEDV S1 spike protein with adjuvants alone (Group C) are capable of inducing IgG, the IgG titers are not comparable to that obtained for the composition of Group D. These results suggest that when the inactivated PEDV and the PEDV S1 spike protein are both included in a single composition, a synergistic effect of further enhancing the IgG levels can be achieved.

To quantitate IgA in the collected stools and intestines, the collected stools were immersed in 0.4 mL of 1× PBS (phosphate buffered saline) and placed at 4° C. for 4 hours. The stools were then grinded into a slurry and then centrifuged at 20,000×g for 10 minutes at 4° C., and the supernatant was collected. The above process was repeated until all the stools have been processed and the supernatant collected. The supernatant was then stored at −20° C. until use. Whereas the collected intestines were processed as follows. After sacrificing the mice, the section of the large intestine to the anus of the mice were taken out and segmented. The segmented intestines were added into 0.4 mL of 1× PBS (phosphate buffered saline) and kept at 4° C. for 4 hours. The segmented intestines were then grinded into a slurry and then centrifuged at 20,000×g for 10 minutes, and the supernatant was collected. The above process was repeated until all the collected intestines have been processed and the supernatant collected. The supernatant was then stored at −20° C. until use.

For ELISA, RECOMBINANT PEDV S1 protein was added at a concentration of 200 ng/well using coating buffer A for coating onto an ELISA microplate. The microplate was kept at 4° C. overnight, and then washed with 1× PBST for four times. Subsequently, 250 μL of blocker (5% skim milk) was added to each of the wells and kept at room temperature for 1 hour. The microplate was then washed with 1× PBST for four times. The collected supernatant samples (100 μL; diluted 2 times for both the supernatant of stools and intestines) were then added to each of the wells and kept at 37° C. for 1 hour. Subsequently, 100 μL of secondary antibody (Mouse-IgA-HRPO, diluted 5000 times) was added to each of the wells and kept at 37° C. for 1 hour. The microplate was then washed with 1× PBST for four times, and 100 μL of 3,3',5,5'-Tetramethylbenzidine (TMB) was added to each of the wells to allow color development for 10 minutes at room temperature. Thereafter, the reaction was terminated by adding 100 μL of stop solution to each of the wells, and the amount of IgA in the supernatant samples was quantitated using an ELISA reader at 450 nm. The evaluation results are presented in FIG. 2B.

Figure 2B:
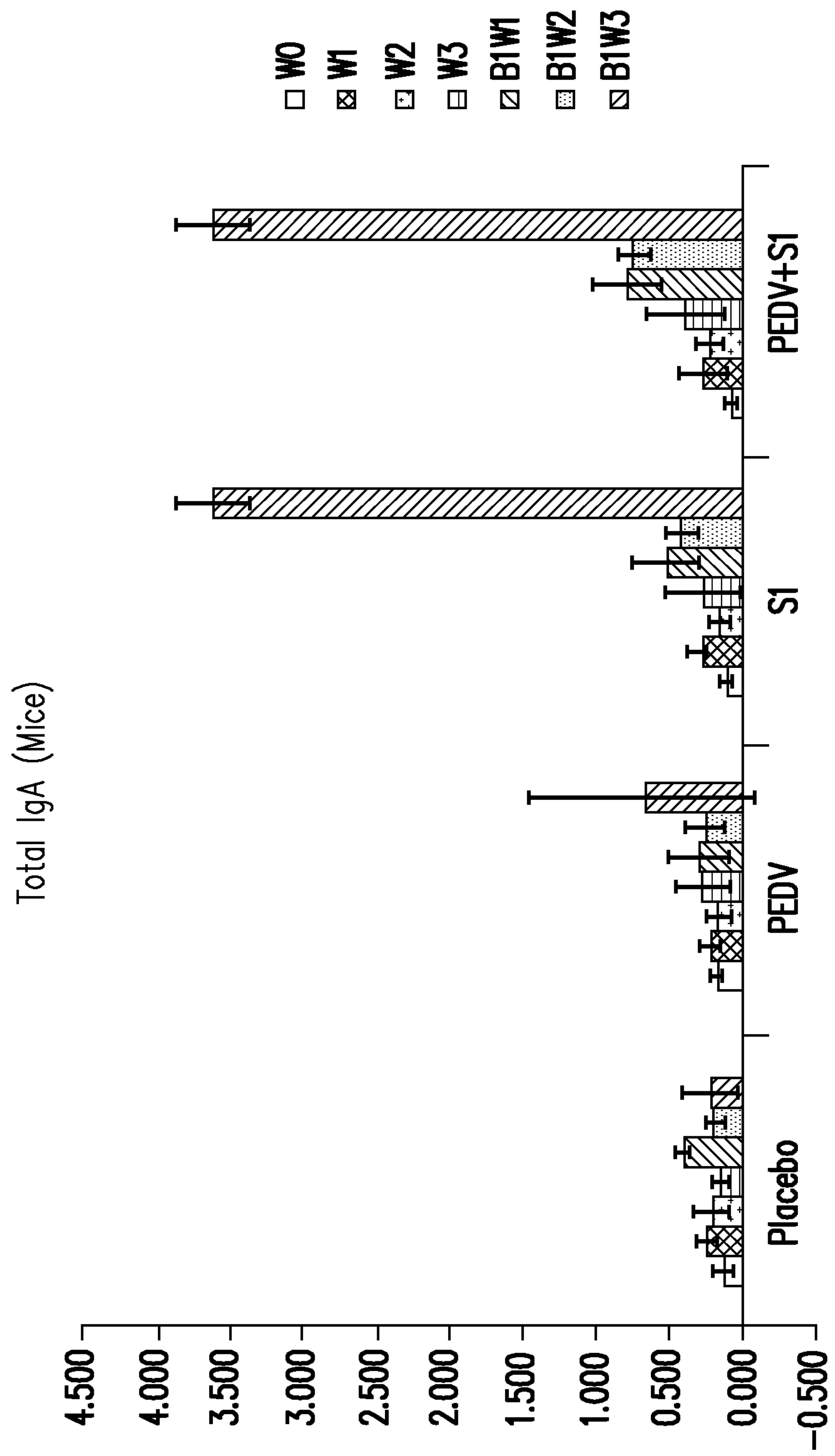
FIG. 2B illustrates the results from ELISA for detecting the presence of IgA in mice for different test groups from Example 2.

FIG. 2B illustrates the results from ELISA for detecting the presence of IgA in mice for different test groups from Example 2. Referring to FIG. 2B, the increase of the detected IgA levels was most apparent in Group C (S1) and Group D (PEDV+S1) after the the second vaccination. However, the increase in the IgA levels was slightly higher in Group D after the second vaccination. In comparison, inactivated PEDV with adjuvants alone (Group B) seems to be unsuccessful in inducing IgA, and showed IgA levels that are similar to the control (Group A). In addition, although PEDV S1 spike protein with adjuvants alone (Group C) are capable of inducing IgA, the IgA levels further increased when the inactivated PEDV was used together in the composition (Group D). These results suggest that the inactivated PEDV and the PEDV S1 spike protein play a mutual role in the enhancement of the IgA levels.

The neutralizing antibody titers in the collected serums of the mice from Groups A to D were evaluated as follows. In brief, a PEDV infection medium (PI medium) was first prepared by adding 20 mL of 15% of Tryptose phosphate broth and 10 mL of 2% yeast extract into 970 mL of Dulbecco's Modified Eagle's Medium (DMEM), and then thoroughly mixed. Thereafter, 1 mL of Trypsin (10 mg/mL) was added to the mixture, and stored at 4° C. until use. For the neutralizing antibody assay, the serum samples of the mice were heated at 56° C. for 30 minutes to inactivate complement prior to use. For each well, mixtures containing 60 μL of PEDVPT virus and 60 μL of 2-fold diluted serum samples in the PI medium were incubated at 37° C. for 1 hour. The mixtures were then applied to Vero cells ($2*10^4$/well) seeded in 96-well plate and incubated for 1 hour. The Vero cells were then washed twice and maintained in the PI medium for 24 hours. Cytopathic effects were detected using inverted light microscopy, and the neutralizing antibody titers were defined as the highest dilution without cytopathic effects. The evaluation results are presented in FIG. 2C.

Figure 2C:
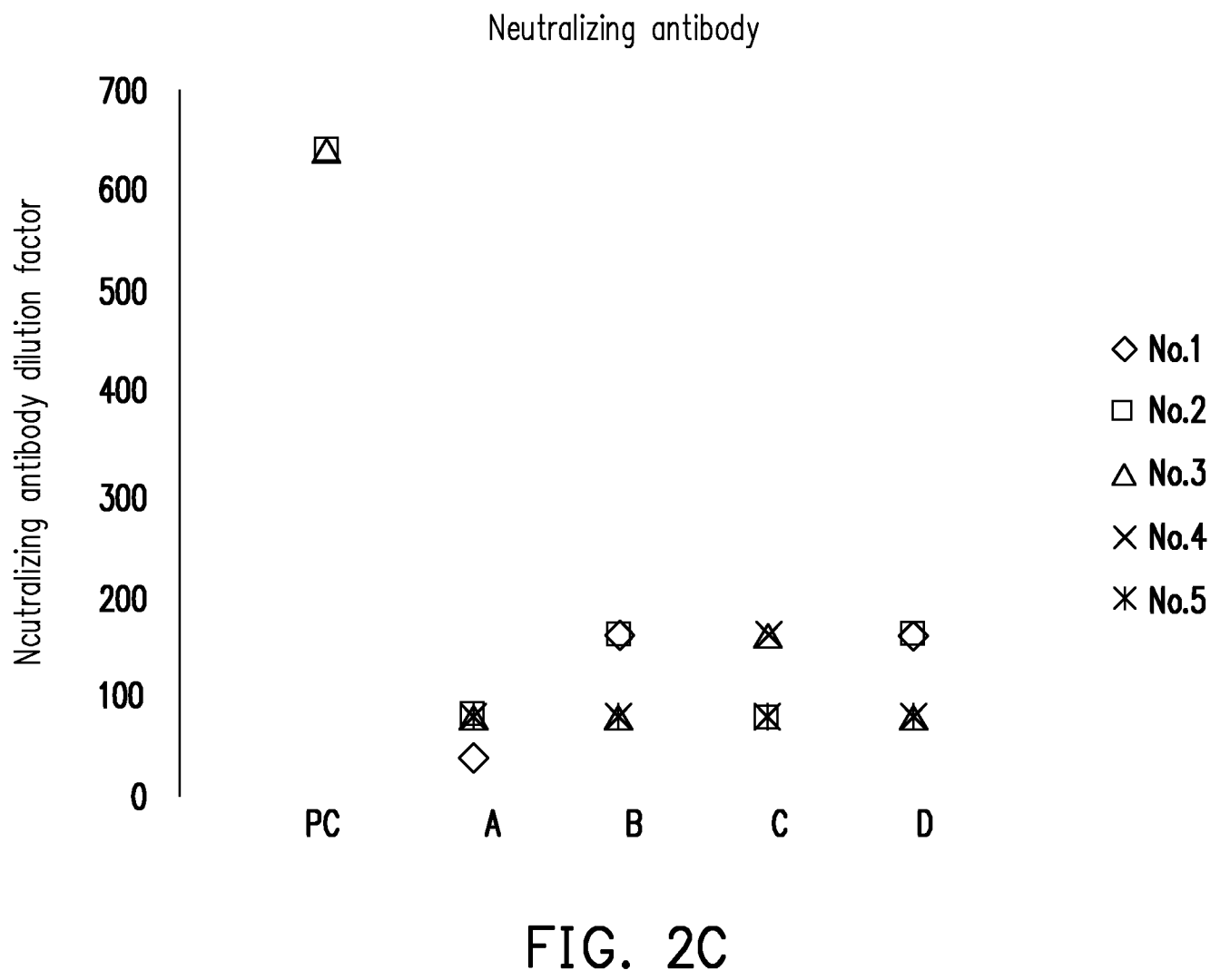

FIG. 2C illustrates the results of detecting the presence of neutralizing antibody in mice for different test groups from Example 2. As illustrated in FIG. 2C, it can be seen that the neutralizing antibody titers are higher in Groups B, C and D, whereas the neutralizing antibody titers are lowest in Group A (Placebo). However, no significant difference was observed in the neutralizing antibody titers between Groups B, C and D. These results suggest that the vaccine composition of the present disclosure (combination of inactivated PEDV and PEDV S1 spike protein) is capable of inducing neutralizing antibody. However, inactivated PEDV and PEDV S1 spike protein alone are also capable of inducing the same neutralizing antibody titers in mice.

According to the above embodiments, the vaccine composition of the present disclosure is capable of inducing systemic Immunoglobulin G (IgG), Immunoglobulin A (IgA) and neutralizing antibody, hence providing sufficient immune protection against PEDV. In addition, a synergistic effect of further enhancing the IgG and IgA levels was observed when at least the inactivated PEDV and PEDV S1 spike protein components are used together in a single composition.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A vaccine composition, comprising:

component (A): a modified porcine epidemic diarrhea virus (PEDV) S1 spike protein encoded with a nucleotide sequence consisting of SEQ ID NO: 3;

component (B): an inactivated porcine epidemic diarrhea virus (PEDV) comprising the nucleotide sequence of SEQ ID NO: 4, wherein the component (A) and the component (B) are separate components; and mineral oil-based adjuvants.

2. The vaccine composition according to claim 1, wherein a concentration of the mineral oil-based adjuvants is in a range of 55% by weight to 65% by weight based on a total weight of the vaccine composition.

3. The vaccine composition according to claim 1, wherein a concentration of the PEDV S1 spike protein is in a range from 20μg /dose to 40μg/dose.

4. The vaccine composition according to claim 1, wherein a concentration of the PEDV S1 spike protein is 30 μg/dose.

5. The vaccine composition according to claim 1, wherein a concentration of the inactivated PEDV is in a range from $1*10^6$ of 50% tissue culture infective dose ($TCID_{50}$)/dose to $1*10^9$ $TCID_{50}$/dose.

6. The vaccine composition according to claim 1, wherein a concentration of the inactivated PEDV is in a range from $1*10^6$ of $TCID_{50}$/dose to $1*10^7$ $TCID_{50}$/dose.

7. A method of using the vaccine composition according to claim 1 for preventing porcine epidemic diarrhea virus (PEDV) infection in swine, comprising:

vaccinating a pregnant sow by administering a first dose of the vaccine composition eight weeks prior to farrowing;

vaccinating the pregnant sow by administering a second dose of the vaccine composition five weeks prior to farrowing; and vaccinating the pregnant sow by administering a third dose of the vaccine composition three weeks prior to farrowing.

* * * * *